US012582359B2

(12) United States Patent
Hirokawa

(10) Patent No.: US 12,582,359 B2
(45) Date of Patent: Mar. 24, 2026

(54) IMAGE DISPLAY METHOD, STORAGE MEDIUM, AND IMAGE DISPLAY DEVICE

(71) Applicant: NIKON CORPORATION, Tokyo (JP)

(72) Inventor: Mariko Hirokawa, Yokohama (JP)

(73) Assignee: NIKON CORPORATION, Tokyo (JP)

( * ) Notice: Subject to any disclaimer, the term of this patent is extended or adjusted under 35 U.S.C. 154(b) by 0 days.

(21) Appl. No.: 18/523,655

(22) Filed: Nov. 29, 2023

(65) Prior Publication Data

US 2024/0090850 A1    Mar. 21, 2024

Related U.S. Application Data

(63) Continuation of application No. 17/884,049, filed on Aug. 9, 2022, now Pat. No. 11,864,929, which is a continuation of application No. 16/668,737, filed on Oct. 30, 2019, now abandoned.

(51) Int. Cl.
| | |
|---|---|
| *G06K 9/00* | (2022.01) |
| *A61B 3/00* | (2006.01) |
| *A61B 5/00* | (2006.01) |
| *G06T 7/00* | (2017.01) |

(52) U.S. Cl.
CPC .......... *A61B 5/7425* (2013.01); *A61B 3/0025* (2013.01); *A61B 5/004* (2013.01); *A61B 5/0073* (2013.01); *G06T 7/0014* (2013.01); *G06T 2207/10101* (2013.01); *G06T 2207/30041* (2013.01)

(58) Field of Classification Search
None
See application file for complete search history.

(56) References Cited

U.S. PATENT DOCUMENTS

| | | | |
|---|---|---|---|
| 9,039,183 B2 | 5/2015 | Muyo et al. | |
| 2008/0151187 A1 | 6/2008 | Tsukada et al. | |
| 2012/0189184 A1* | 7/2012 | Matsumoto | A61B 3/102 |
| | | | 382/131 |
| 2018/0303667 A1 | 10/2018 | Peyman | |
| 2019/0115964 A1 | 4/2019 | Yum et al. | |
| 2020/0390330 A1 | 12/2020 | Fukuma et al. | |
| 2021/0104313 A1 | 4/2021 | Mizobe et al. | |
| 2021/0398259 A1 | 12/2021 | Yamazoe et al. | |

FOREIGN PATENT DOCUMENTS

| | | |
|---|---|---|
| JP | 2008-154704 A | 7/2008 |
| JP | 2019-154825 A | 9/2019 |
| WO | WO-2019/240257 A1 | 12/2019 |

OTHER PUBLICATIONS

Non-Final Office Action on U.S. Appl. No. 16/668,737 DTD Mar. 9, 2022.

(Continued)

*Primary Examiner* — Wei Wen Yang
(74) *Attorney, Agent, or Firm* — Foley & Lardner LLP

(57) ABSTRACT

An image display method executed by a processor comprises displaying a screen including a two-dimensional fundus image of an examined eye and a three-dimensional eyeball image of the examined eye, finding a second region in the three-dimensional eyeball image that corresponds to a first region specified in the two-dimensional fundus image, and displaying a mark indicating the second region in the three-dimensional eyeball image.

2 Claims, 27 Drawing Sheets

(56)         References Cited

OTHER PUBLICATIONS

Office Action issued in corresponding Japanese Patent Application No. 2018-191914, dated May 10, 2022.
US Non-Final Office Action on U.S. Appl. No. 17/884,049 dated Jan. 19, 2023 (10 pages).
US Notice of Allowance on U.S. Appl. No. 17/884,049 dated Aug. 30, 2023 (7 pages).

* cited by examiner

CPU

IMAGE PROCESSING SECTION — 182

DISPLAY CONTROL SECTION — 184

PROCESSING SECTION — 186

(1)

250A2    250A    252    250B2   250B     172A

250A1     250B1

(SLO IMAGE DISPLAY AREA)

(THREE-DIMENSIONAL
IMAGE DISPLAY AREA)

Figure 19B:
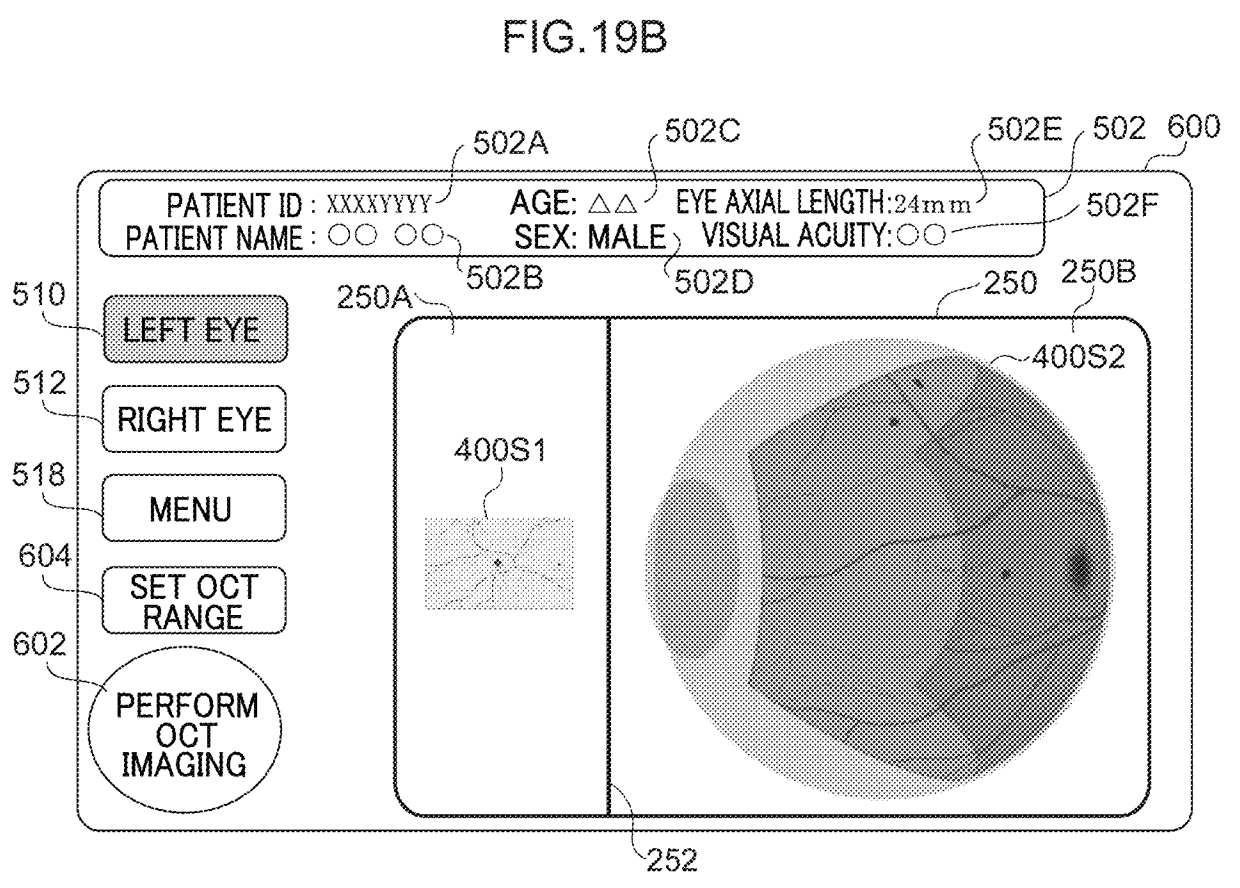

PATIENT ID : XXXXYYYY　○○ ○○
PATIENT NAME : ○○ ○○

AGE : △△　EYE AXIAL LENGTH : 24mm ○○
SEX : MALE　VISUAL ACUITY : ○○

502A
502B
502C
502D
502E
502F
502
600
250B
250
250A

400S2
400S1
252

LEFT EYE
RIGHT EYE
MENU
SET OCT RANGE
PERFORM OCT IMAGING 510
512
518
604
602

IMAGE DISPLAY METHOD, STORAGE MEDIUM, AND IMAGE DISPLAY DEVICE

CROSS-REFERENCE TO RELATED APPLICATION

This application is a continuation of U.S. patent application Ser. No. 17/884,049, filed Aug. 9, 2022, which is a continuation of U.S. patent application Ser. No. 16/668,737, filed Oct. 30, 2019, and is based on Japanese Patent Application No. 2018-191914 filed on Oct. 10, 2018, the disclosures of which are incorporated by reference herein in their entireties.

BACKGROUND

Technical Field

The technology disclosed herein relates to an image display method, a storage medium, and an image display device.

Related Art

US Patent Application Laid-Open No. 2009/0115964A1 discloses an ophthalmic imaging device in which a tomographic image acquisition position is set on a displayed fundus observation image. It would be desirable to display the tomographic image acquisition position on an image of the fundus.

SUMMARY

A first aspect of the present disclosure is an image display method executed by a processor comprising displaying a display screen including a two-dimensional image of an examined eye and a three-dimensional image of the examined eye, determining a second region in the three-dimensional image that corresponds to a first region specified by a first mark in the two-dimensional image, and displaying a second mark indicating the second region in the three-dimensional image.

A second aspect of the present disclosure is an image display method executed by a processor, the image display method comprising displaying a display screen including a two-dimensional image of an examined eye and a three-dimensional image of the examined eye, finding determining a second region in the two-dimensional image that corresponds to a first region specified by a first mark in the three-dimensional image, and displaying a second mark indicating the second region in the two-dimensional image.

A third aspect of the present disclosure is a storage medium being not transitory signal and stored with an image display program that causes a computer to execute processing, the processing comprising displaying a display screen including a two-dimensional image of an examined eye and a three-dimensional image of the examined eye, determining a second region in the three-dimensional image that corresponds to a first region specified by a first mark in the two-dimensional image, and displaying a second mark indicating the second region in the three-dimensional image.

A fourth aspect of the present disclosure is a storage medium being not transitory signal and stored with an image display program that causes a computer to execute processing, the processing comprising displaying a display screen including a two-dimensional image of an examined eye and a three-dimensional image of the examined eye, determining a second region in the two-dimensional image that corresponds to a first region specified by a first mark in the three-dimensional image, and displaying a second mark indicating the second region in the two-dimensional image.

A fifth aspect of the present disclosure is an image display device comprising a display section and a processor, wherein the processor is configured to display a display screen including a two-dimensional image of an examined eye and a three-dimensional image of the examined eye on the display section, determine a second region in the three-dimensional image that corresponds to a first region specified by a first mark in the two-dimensional image, and display a second mark indicating the second region in the three-dimensional image on the display section.

A sixth aspect of the present disclosure is an image display device comprising a display section and a processor, wherein the processor is configured to display a display screen including a two-dimensional image of an examined eye and a three-dimensional image of the examined eye on the display section, determine a second region in the two-dimensional image that corresponds to a first region specified by a first mark in the three-dimensional image, and display a second mark indicating the second region in the two-dimensional image on the display section.

BRIEF DESCRIPTION OF THE DRAWINGS

Exemplary embodiments of the present invention will be described in detail based on the following figures, wherein:

FIG. 6 is a block diagram illustrating functionality of a CPU included in the management server illustrated in FIG. 5;

FIG. 11C is a schematic diagram illustrating display contents of an examined eye check screen in a state displayed on a display of an image viewer;

FIG. 18 is a diagram illustrating a 2D/3D display screen;

FIG. 19A is a diagram illustrating a 2D/3D display screen, in which display of a UWF-SLO fundus image has been magnified, and display of a three-dimensional image has been shrunk on the 2D/3D display screen;

FIG. 19B is a diagram illustrating a 2D/3D display screen, in which display of a UWF-SLO fundus image has been shrunk, and display of a three-dimensional image has been magnified on the 2D/3D display screen;

DETAILED DESCRIPTION

First Exemplary Embodiment

Figure 1:
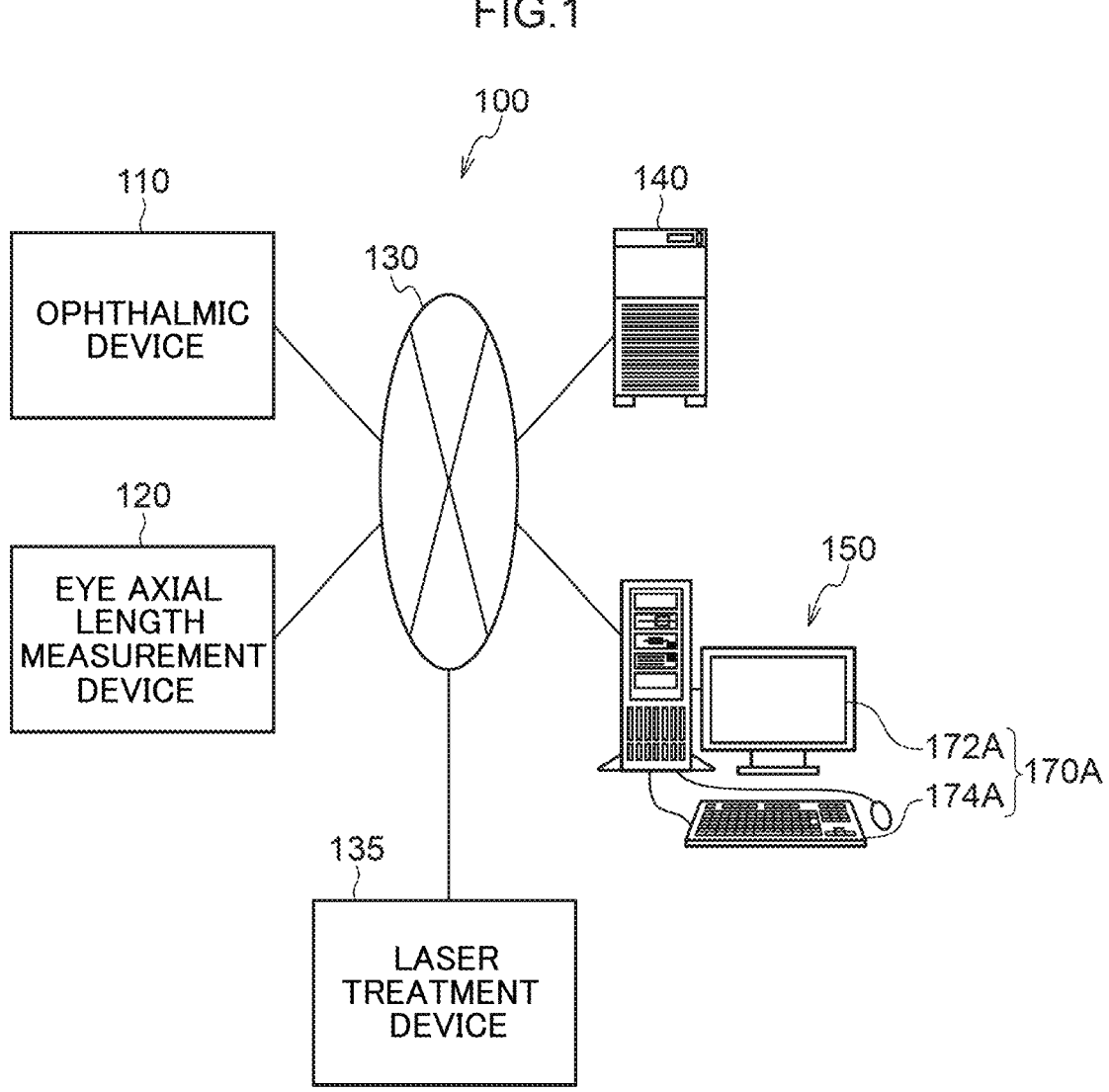
FIG. 1 is a schematic diagram illustrating an overall configuration of an ophthalmic system.

Explanation follows regarding configuration of an ophthalmic system 100, with reference to FIG. 1. As illustrated in FIG. 1, the ophthalmic system 100 includes an ophthalmic device 110, an eye axial length measurement device 120, a management server device (referred to hereafter as "management server") 140, an image display device (referred to hereafter as "image viewer") 150, and a laser treatment device 135. The ophthalmic device 110 acquires an image of the fundus. The eye axial length measurement device 120 measures the axial length of the eye of a patient. The management server 140 stores plural fundus images, eye axial lengths, and tomographic images obtained by imaging the fundus of plural patients using the ophthalmic device 110, and stores these in association with patient IDs. The image viewer 150 displays fundus images acquired from the management server 140. The laser treatment device 135 performs laser treatment on an examined eye of a patient. Examples of such laser treatment include laser photocoagulation in which a laser beam of a particular wavelength is shone onto a region of the fundus, or photodynamic therapy.

The ophthalmic device 110, the eye axial length measurement device 120, the management server 140, and the image viewer 150 are coupled together over a network 130.

The eye axial length measurement device 120 has two eye axial length measurement modes for measuring eye axial length, this being the length of an examined eye 12 in an eye axial direction: a first mode and a second mode. The first mode is a mode in which after light from a non-illustrated light source is guided into the examined eye 12, interference between light reflected from the fundus and light reflected from the cornea is photo-detected as interference light, and the eye axial length is measured based on an interference signal representing the photo-detected interference light. The second mode is a mode to measure the eye axial length by employing non-illustrated ultrasound waves.

The eye axial length measurement device 120 transmits the eye axial length as measured using either the first mode or the second mode to the management server 140. The eye axial length may be measured using both the first mode and the second mode, and in such cases, an average of the eye axial lengths as measured using the two modes is transmitted to the management server 140 as the eye axial length.

Figure 2:
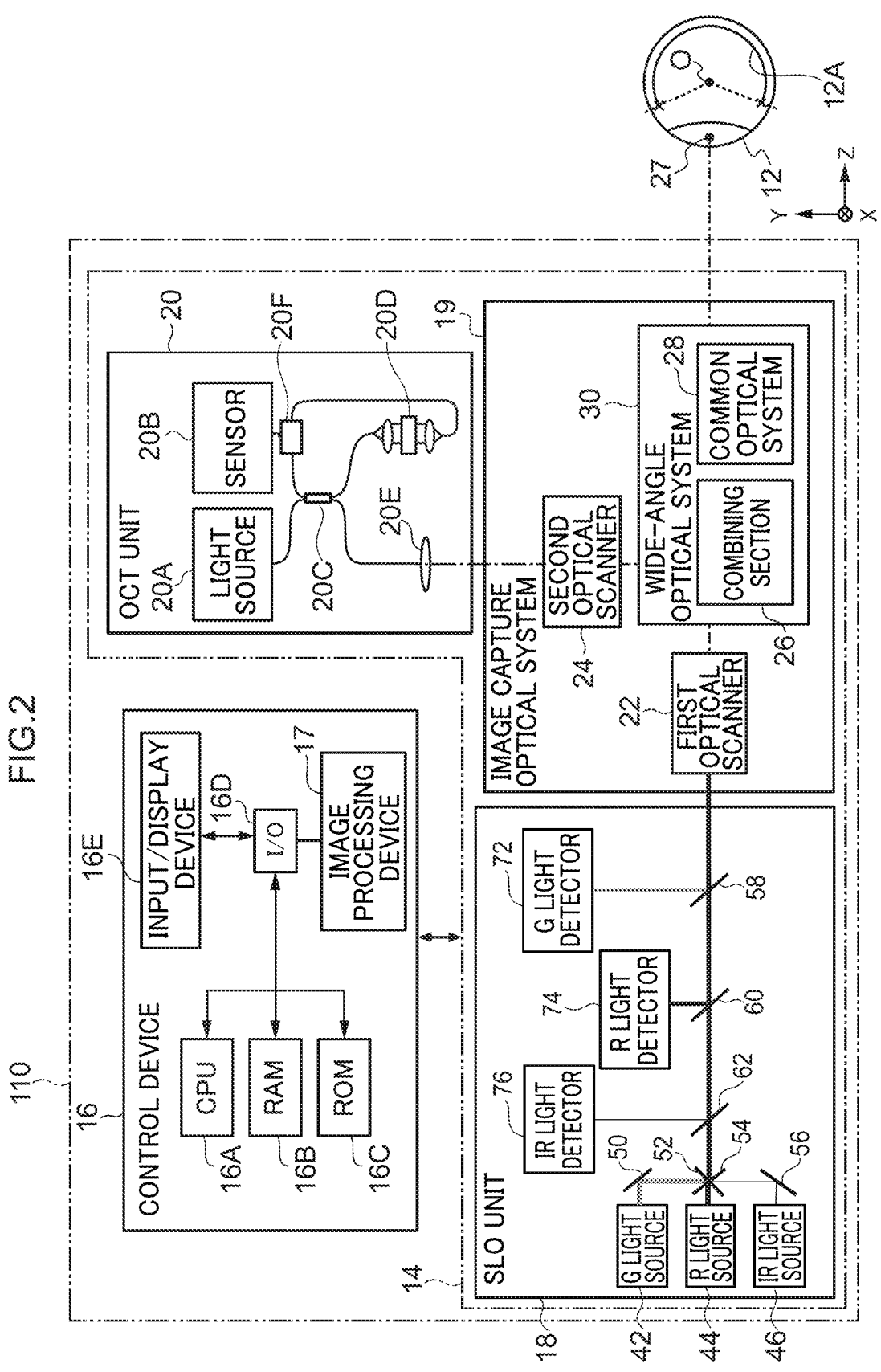
FIG. 2 is a block diagram illustrating a schematic configuration of an ophthalmic device included in an ophthalmic system.

Explanation follows regarding configuration of the ophthalmic device 110, with reference to FIG. 2. In the present specification, for ease of explanation, scanning laser ophthalmoscope is abbreviated to SLO, and optical coherence tomography is abbreviated to OCT.

The ophthalmic device 110 includes an imaging device 14 and a control device 16. The imaging device 14 is provided with an SLO unit 18, an image capture optical system 19, and an OCT unit 20, and acquires a fundus image of the fundus of the examined eye 12. Two-dimensional fundus images that have been acquired by the SLO unit 18 are referred to hereafter as SLO fundus images. Tomographic images, face-on images (en-face images) and the like of the retina created based on OCT data acquired by the OCT unit 20 are referred to hereafter as OCT images.

The control device 16 includes a computer provided with a Central Processing Unit (CPU) 16A, Random Access Memory (RAM) 16B, Read-Only Memory (ROM) 16C, and an input/output (I/O) port 16D.

The control device 16 is provided with an input/display device 16E coupled to the CPU 16A through the I/O port 16D. The input/display device 16E includes a graphical user interface to display images of the examined eye 12 and to receive various instructions from a user. An example of the graphical user interface is a touch panel display.

The control device 16 is also provided with an image processing device 17 coupled to the I/O port 16D. The image processing device 17 generates images of the examined eye 12 based on data acquired by the imaging device 14. Note that the control device 16 is coupled to the network 130 through a communication interface, not illustrated in the drawings.

Figure 3:
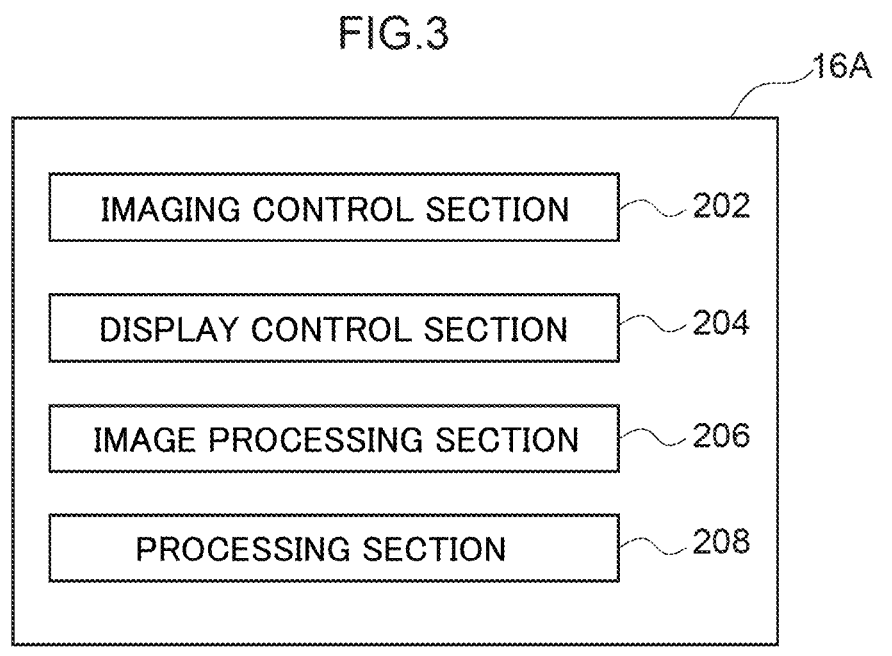
FIG. 3 is a block diagram illustrating functionality of a CPU included in the ophthalmic device illustrated in FIG. 2.

Explanation follows regarding various functions implemented by the CPU 16A of the control device 16 executing a processing program, with reference to FIG. 3. The processing program is stored in the ROM 16C or the RAM 16B, and is read at an initial setting timing or on startup. Note that configuration may be made in which a non-illustrated storage device (hard disk or the like) is provided, and the processing program is stored on the non-illustrated storage device and read at an initial setting timing or on startup.

The processing program includes an image capture control function, a display control function, an image processing function, and a processing function. As illustrated in FIG. 3, the CPU 16A functions as an image capture control section 202, a display control section 204, an image processing section 206, and a processing section 208 by the CPU 16A executing the processing program that includes these functions.

Although the control device 16 of the ophthalmic device 110 is provided with the input/display device 16E as illustrated in FIG. 2, the technology disclosed herein is not limited thereto. For example, a configuration may be adopted in which the control device 16 of the ophthalmic device 110 is not provided with the input/display device 16E, and instead a separate input/display device is provided that is physically independent of the ophthalmic device 110. In such cases, the display device may be provided with an image processing processor unit that operates under the control of the display control section 204 of the CPU 16A in the control device 16. Such an image processing processor unit may display SLO fundus images and the like based on an image signal output as an instruction by the display control section 204.

The imaging device 14 operates under the control of the imaging control section 202 of the control device 16. The imaging device 14 includes the SLO unit 18, the image capture optical system 19, and the OCT unit 20. The image capture optical system 19 includes a first optical scanner 22, a second optical scanner 24, and a wide-angle optical system 30.

The first optical scanner 22 scans light emitted from the SLO unit 18 two dimensionally in the X direction and the Y direction. The second optical scanner 24 scans light emitted from the OCT unit 20 two dimensionally in the X direction and the Y direction. As long as the first optical scanner 22 and the second optical scanner 24 are optical elements capable of polarizing light beams, they may be configured by any out of polygon mirrors, mirror galvanometers, or the like. A combination thereof may also be employed.

The wide-angle optical system 30 includes an objective optical system (not illustrated in FIG. 2) provided with a common optical system 28, and a combining section 26 that combines light from the SLO unit 18 with light from the OCT unit 20

The objective optical system of the common optical system 28 may be a reflection optical system employing a concave mirror such as an elliptical mirror, a refraction optical system employing a wide-angle lens, or may be a reflection-diffraction optical system employing a combination of a concave mirror and a lens. Employing a wide-angle optical system that utilizes an elliptical mirror, a wide-angle lens, or the like enables imaging of not only a central portion of the fundus, but also of the retina at the periphery of the fundus.

For a system employing an elliptical mirror, a configuration may be adopted that utilizes an elliptical mirror system as disclosed in International Patent Application Nos. PCT/JP2014/084619 or PCT/JP2014/084630. The respective disclosures of International Patent Application No. PCT/JP2014/084619 (International Publication (WO) No. 2016/103484), internationally filed on Dec. 26, 2014, and International Patent Application No. PCT/JP2014/084630 (WO No. 2016/103489), internationally filed on Dec. 26, 2014, are incorporated in their entirety by reference herein.

Observation of the fundus over a wide field of view (FOV) 12A is implemented by employing the wide-angle optical system 30. The FOV 12A refers to a range capable of being imaged by the imaging device 14. The FOV 12A may be expressed as a viewing angle. In the present exemplary embodiment the viewing angle may be defined in terms of an internal illumination angle and an external illumination angle. The external illumination angle is the angle of illumination by a light beam shone from the ophthalmic device 110 toward the examined eye 12, and is an angle of illumination defined with respect to a pupil 27. The internal illumination angle is the angle of illumination of a light beam shone onto the fundus F, and is an angle of illumination defined with respect to an eyeball center O. A correspondence relationship exists between the external illumination angle and the internal illumination angle. For example, an external illumination angle of 120° is equivalent to an internal illumination angle of approximately 160°. The internal illumination angle in the present exemplary embodiment is 200°.

SLO fundus images obtained by imaging at an imaging angle having an internal illumination angle of 160° or greater are referred to as UWF-SLO fundus images. UWF is an abbreviation of Ultra Wide Field.

An SLO system is realized by the control device 16, the SLO unit 18, and the image capture optical system 19 as illustrated in FIG. 2. The SLO system is provided with the wide-angle optical system 30, enabling fundus imaging over the wide FOV 12A.

The SLO unit 18 is provided with a green (G) light source 42, a red (R) light source 44, an infrared (for example near infrared) (IR) light source 46, and optical systems 50, 52, 54, 56 to guide the light from the light sources 42, 44, 46 onto a single optical path using reflection or transmission. The optical systems 50, 56 are configured by mirrors, and the optical systems 52, 54 are configured by beam splitters. G light is reflected by the optical systems 50, 54, R light is transmitted through the optical systems 52, 54, and IR light is reflected by the optical systems 52, 56. The respective lights are thereby guided onto a single optical path.

The SLO unit 18 is configured so as to be capable of switching between a light source or a combination of light sources employed for emitting light, such as a mode in which R light and G light are emitted, a mode in which infrared light is emitted, etc. Although FIG. 2 includes three light sources, i.e. the G light source 42, the R light source 44, and the IR light source 46, the technology disclosed herein is not limited thereto. For example, the SLO unit 18 may also include a blue (B) light source or a white light source, in a configuration in which light is emitted in various modes, such as a mode in which G light, R light, and B light are emitted or a mode in which white light is emitted alone.

Light introduced to the image capture optical system 19 from the SLO unit 18 is scanned in the X direction and the Y direction by the first optical scanner 22. The scanning light passes through the wide-angle optical system 30 and the pupil 27 and is shone onto the fundus. Reflected light that has been reflected by the fundus passes through the wide-angle optical system 30 and the first optical scanner 22 and is introduced into the SLO unit 18. The SLO unit 18 is provided with a beam splitter 58 that, from out of the light from a posterior portion (the fundus) of the examined eye 12, reflects G light therein and transmits light other than G light therein. The SLO unit 18 is further provided with a beam splitter 60 that, from out of the light transmitted through the beam splitter 58, reflects R light therein and transmits light other than R light therein. The SLO unit 18 is further provided with a beam splitter 62 that reflects IR light from out of the light transmitted through the beam splitter 60. The SLO unit 18 is further provided with a G light detector 72 to detect G light reflected by the beam splitter 58, an R light detector 74 to detect R light reflected by the beam splitter 60, and an IR light detector 76 to detect IR light reflected by the beam splitter 62.

In the case of G light, light that has passed through the wide-angle optical system 30 and the first optical scanner 22 and been introduced into the SLO unit 18 (i.e. reflected light that has been reflected by the fundus) is reflected by the beam splitter 58 and photo-detected by the G light detector 72. In the case of R light, the incident light is transmitted through the beam splitter 58, reflected by the beam splitter 60, and photo-detected by the R light detector 74. In the case of IR light, the incident light is transmitted through the beam splitters 58, 60, reflected by the beam splitter 62, and photo-detected by the IR light detector 76. The image processing device 17 that operates under the control of the image processing section 206 generates SLO fundus images based on signals detected by the G light detector 72, the R light detector 74, and the IR light detector 76.

An OCT system is realized by the control device 16, the OCT unit 20, and the image capture optical system 19 illustrated in FIG. 2. The OCT system is provided with the wide-angle optical system 30. This enables fundus imaging to be performed over the wide FOV 12A similarly to when imaging the SLO fundus images as described above. The OCT unit 20 includes a light source 20A, a sensor (detector) 20B, a first light coupler 20C, a reference optical system 20D, a collimator lens 20E, and a second light coupler 20F.

Light emitted from the light source 20A is split by the first light coupler 20C. After one part of the split light has been collimated by the collimator lens 20E into parallel light, to serve as measurement light, the parallel light is introduced into the image capture optical system 19. The measurement light is scanned in the X direction and the Y direction by the second optical scanner 24. The scanned light is shone onto the fundus through the wide-angle optical system 30 and the pupil 27. Measurement light that has been reflected by the fundus passes through the wide-angle optical system 30 and the second optical scanner 24 so as to be introduced into the OCT unit 20. The measurement light then passes through the collimator lens 20E and the first light coupler 20C before being introduced into the second light coupler 20F.

The other part of the light emitted from the light source 20A and split by the first light coupler 20C is introduced into the reference optical system 20D as reference light, and is introduced into the second light coupler 20F through the reference optical system 20D.

The respective lights that are introduced into the second light coupler 20F, namely the measurement light reflected by the fundus and the reference light, interfere with each other in the second light coupler 20F so as to generate interference light. The interference light is photo-detected by the sensor 20B. The image processing device 17 operating under the control of the image processing section 206 generates OCT images, such as tomographic images and en-face images, based on OCT data detected by the sensor 20B.

Note that although in the present exemplary embodiment an example is given in which the light source 20A is a swept-source OCT (SS-OCT), the light source 20A may be from various OCT systems, such as from of a spectral-domain OCT (SD-OCT) or a time-domain OCT (TD-OCT) system.

Figure 4:
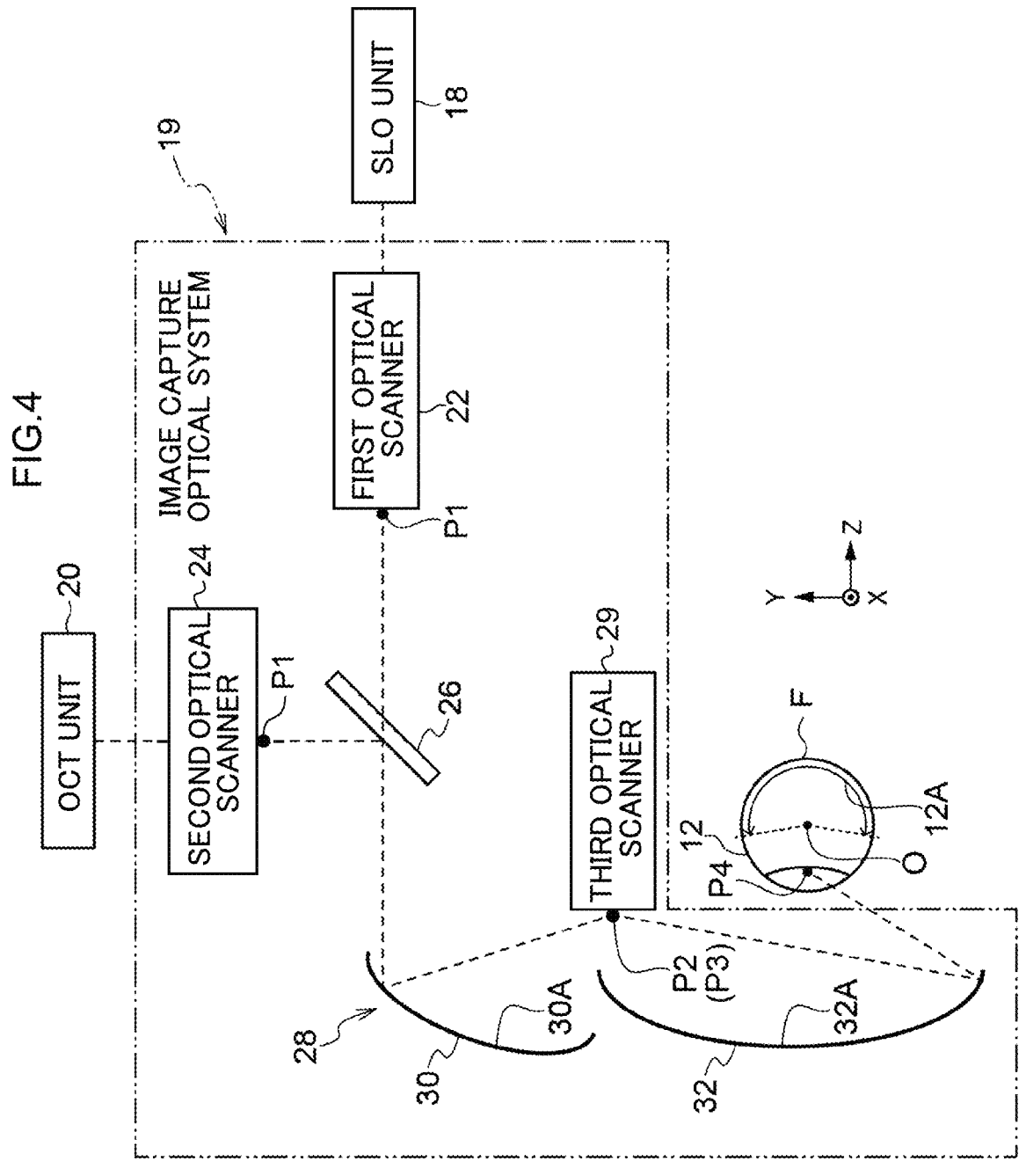
FIG. 4 is a schematic configuration diagram illustrating configuration of relevant portions of an image capture optical system of an ophthalmic device included in an ophthalmic system.

Detailed explanation follows regarding configuration of the image capture optical system 19 included in the ophthalmic device 110, with reference to FIG. 4. As illustrated in FIG. 4, the common optical system 28 includes elliptical mirrors 30, 32, and a third optical scanner 29 disposed between the two elliptical mirrors 30, 32. The elliptical mirrors 30, 32 include reflective surfaces 30A, 32A configured by what are referred to as spheroidal faces. Each of the spheroidal faces is a face formed by rotating an ellipse about an axis joining the two focal points of the ellipse. FIG. 4 illustrates a section of each ellipse.

As described above, since the first optical scanner 22 and the second optical scanner 24 each scan rays in the Y direction (within the plane of the drawings), the elliptical mirror 30 only reflects scanning light in the Y direction, and therefore may have a narrow width in the X direction. The elliptical mirror 30 thus has a narrow elongated shape extending along the Y direction, being what is referred to as a slit mirror. Conversely, the third optical scanner 29 additionally scans in the X direction (within a plane perpendicular to the plane of the drawings), and therefore the X direction width of the elliptical mirror 32 is a width required in order for the elliptical mirror 32 to pick up the X direction scanning light of the third optical scanner 29. Although the combining section 26 configured by a dichromatic mirror and the like and the elliptical mirrors 30, 32 are illustrated in a side view cross-section in FIG. 4, this is in order to illustrate the placement sequence of their relative positions, and is not strictly accurate.

The elliptical reflective surface 30A of the elliptical mirror 30 has a first focal point P1 and a second focal point P2. The first optical scanner 22 and the second optical scanner 24 are disposed aligned with the first focal point P1, with the combining section 26 configured by a dichromatic mirror and the like interposed therebetween. The third optical scanner 29 is disposed at the second focal point P2. The elliptical reflective surface 32A of the elliptical mirror 32 has two focal points P3, P4. The focal point P3 is aligned with the second focal point P2 of the elliptical reflective surface of the slit mirror, and the center of the pupil of the examined eye 12 is positioned at the position of the focal point P4. Accordingly, the first optical scanner 22, the second optical scanner 24, and the third optical scanner 29 are configured in a conjugated positional relationship with the center of the pupil of the examined eye 12. The image capture optical system 19 configured by combining the two elliptical mirrors 30, 32 and the three optical scanners 22, 24, 29 thus enables the fundus to be scanned by rays over a very wide external illumination angle in either SLO or OCT.

Note that employing elliptical mirrors such as those described is a highly effective way of achieving the common optical system 28. The provision of two elliptical mirrors is not an absolute requirement, and configuration may be made using a single elliptical mirror. For example, the configurations disclosed in WO Nos. 2016/103484 or 2016/103489 may be employed therefor.

Figure 5:
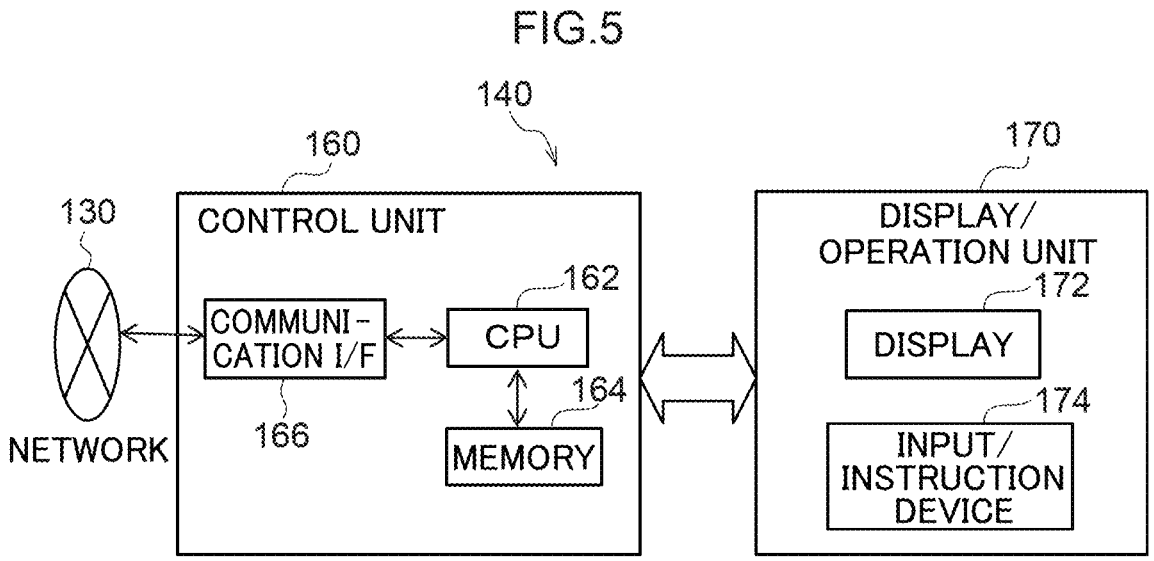
FIG. 5 is a block diagram illustrating configuration of a management server included in an ophthalmic system.

Explanation follows regarding configuration of the management server 140, with reference to FIG. 5. As illustrated in FIG. 5, the management server 140 includes a control unit 160 and a display/operation unit 170. The control unit 160 includes a computer including a CPU 162, memory 164 serving as a storage device, a communication interface (UF) 166, and the like. The display/operation unit 170 is a graphical user interface configured to display images and receive various instructions, and includes a display 172 and an input/instruction device 174 configured by a touch panel or the like.

Figures 24, 25:
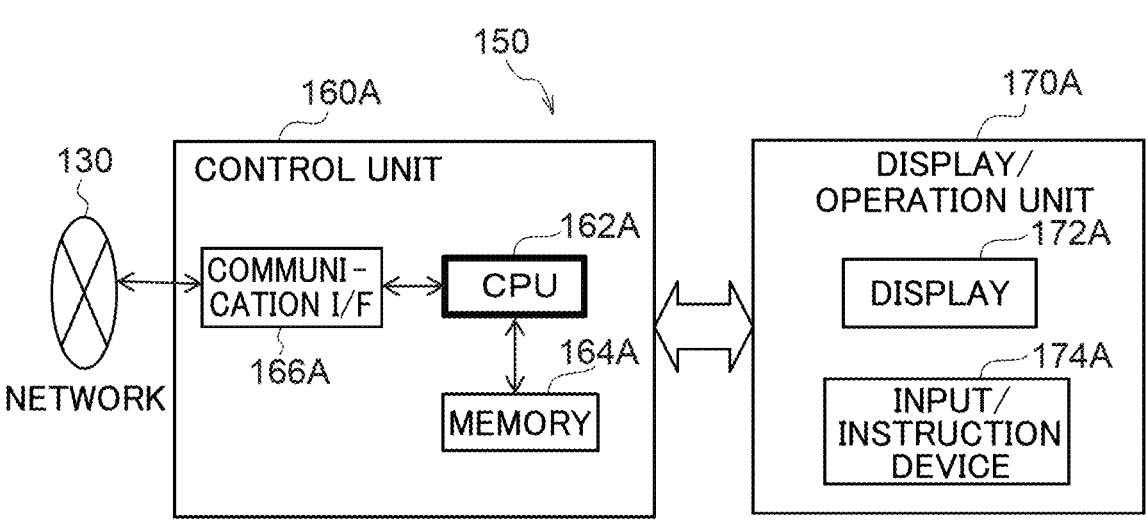
FIG. 24 is a block diagram illustrating configuration of an image viewer included in an ophthalmic system.
FIG. 25 is a block diagram illustrating functionality of a CPU included in the image viewer illustrated in FIG. 24.

The image viewer 150 includes hardware resources that are basically the same as those of the management server 140. As illustrated in FIG. 24, in the image viewer 150, a control unit 160A corresponds to the control unit 160 illustrated in FIG. 5, and a display/operation unit 170A corresponds to the display/operation unit 170 illustrated in FIG. 5. Moreover, as illustrated in FIG. 24, in the control unit 160A, a CPU 162A corresponds to the CPU 162 illustrated in FIG. 5, memory 164A corresponds to the memory 164 illustrated in FIG. 5, and a communication I/F 166A corresponds to the communication I/F 166 illustrated in FIG. 5. Moreover, as illustrated in FIG. 24, in the display/operation unit 170A, a display 172A corresponds to the display 172 illustrated in FIG. 5, and an input/instruction device 174A corresponds to the input/instruction device 174 illustrated in FIG. 5.

Figure 6:
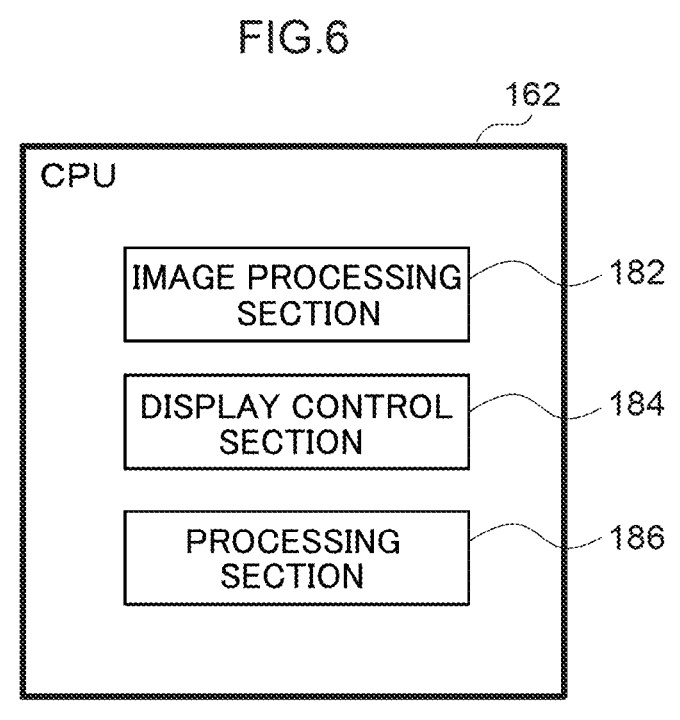

As illustrated in FIG. 25, in the CPU 162A, an image processing section 182A corresponds to an image processing section 182 illustrated in FIG. 6, a display control section 184A corresponds to a display control section 184 illustrated in FIG. 6, and a processing section 186A corresponds to a processing section 186 illustrated in FIG. 6.

The image viewer 150 is an example of an ophthalmic device and an image display device according to the technology disclosed herein. The control unit 160A is an example of a computer according to the technology disclosed herein. The display 172A is an example of a display section according to the technology disclosed herein. The memory 164A stores a control program. The control program stored in the memory 164A is an example of an ophthalmic program and an image display program according to the technology disclosed herein.

Explanation follows regarding various functions implemented by the CPU 162A executing the control program, with reference to FIG. 6. The control program includes an image processing function, a display control function, and a processing function. As illustrated in FIG. 25, the CPU 162A functions as the image processing section 182A, the display control section 184A, and the processing section 186A by the CPU 162A executing the control program that includes these functions.

A storage device 154 stores patient data for each patient. A patient referred to here is an example of a subject of the examination previously described. The patient data is data including a patient ID identifying the patient, two-dimensional image data expressing a two-dimensional image, three-dimensional image data expressing a three-dimensional image, and position correspondence information. In the following explanation, the two-dimensional image data is also referred to as 2D image data for the sake of convenience. Likewise, the three-dimensional image data is also referred to as 3D image data for the sake of convenience.

The position correspondence information is information associating two-dimensional position information representing the positions of pixels in a two-dimensional image with three-dimensional position information representing the positions of corresponding pixels in a three-dimensional image for each of the pixels in the two-dimensional image.

The processing section 186A illustrated in FIG. 25 performs processing required in order to make the CPU 162A operate as the image processing section 182A and the display control section 184. The image processing section 182A is an example of an acquisition section according to the technology disclosed herein. The image processing section 182A and the display control section 184 are examples of an image generation section according to the technology disclosed herein.

The image processing section 182A acquires a two-dimensional image and a three-dimensional image. When a two-dimensional conversion target region has been specified in the two-dimensional image, the display control section 184A displays a two-dimensional conversion target region image representing the two-dimensional conversion target region overlaid on the two-dimensional image. Here, the two-dimensional conversion target region is an example of a region according to the technology disclosed herein, and the above-mentioned two-dimensional conversion target region image is an example of a first image according to the technology disclosed herein. For the sake of convenience, in the following explanation the above-mentioned two-dimensional conversion target region image and a three-dimensional conversion target region image, described later, are both referred to as conversion target region images unless it is necessary to differentiate between the two.

The display control section 184A displays a three-dimensional processed image, resulting from aligning the two-dimensional conversion target region with a corresponding position in the three-dimensional image and converting the two-dimensional conversion target region image, overlaid on the three-dimensional image. In this manner, the two-dimensional conversion target region image is converted aligned with a position in the three-dimensional image corresponding to the two-dimensional conversion target region, such that the three-dimensional processed image is an image geometrically aligned with a position in the three-dimensional image corresponding to the two-dimensional conversion target region. The three-dimensional processed image referred to herein is an example of a second image according to the technology disclosed herein. For the sake of convenience, in the following explanation the above-mentioned two-dimensional conversion target region and a three-dimensional conversion target region, described later, are both referred to as conversion target regions unless it is necessary to differentiate between the two.

In this specification, overlaid display refers not only to display in which one image is superimposed on another image, but also to display in which a display region of one image is embedded with another image.

In cases in which a first pre-set condition or a second pre-set condition has been satisfied, the display control section 184A outputs a rotate-and-display instruction signal instructing rotation and display to the display 172A. The three-dimensional image is thus rotated and displayed such that the three-dimensional processed image is displayed at a position where it can be seen. In other words, in cases in which the first pre-set condition or the second pre-set condition has been satisfied, the display control section 184A controls the display 172A so as to rotate and display the three-dimensional image such that the three-dimensional processed image is displayed at a position where it can be seen.

The first pre-set condition is a condition of the size of the three-dimensional processed image exceeding a threshold value. The threshold value is a predetermined value set as a lower limit value for the size of the three-dimensional processed image below which the three-dimensional processed image could not be seen in its entirety from face-on by a user through the display 172A when the three-dimensional image is displayed in a form reflecting the three-dimensional processed image. The threshold value is a value obtained by testing using an actual device and/or by computer simulations, and the like. The concept of the size of the three-dimensional processed image referred to here includes each of the area and length of the three-dimensional processed image.

The second pre-set condition is a condition of the position of the three-dimensional processed image being outside of a specific range. The specific range refers to a predetermined range set as a range where the three-dimensional processed image can be seen in its entirety from face-on by a user through the display 172A when the three-dimensional image is displayed in a form reflecting the three-dimensional processed image. The specific range is a range obtained by testing using an actual device and/or by computer simulations, and the like.

When a three-dimensional conversion target region has been specified in the three-dimensional image, the display control section 184A displays the three-dimensional conversion target region image representing the three-dimensional conversion target region overlaid on the three-dimensional image. The three-dimensional conversion target region is an example of a region according to the technology disclosed herein, and the three-dimensional conversion target region image described above is an example of a first image according to the technology disclosed herein.

The display control section 184A displays a two-dimensional processed image, resulting from aligning the three-dimensional conversion target region image with a position in the two-dimensional image corresponding to the three-dimensional conversion target region and converting the three-dimensional conversion target region image, overlaid on the two-dimensional image. In this manner, the three-dimensional conversion target region image is converted aligned with a position in the two-dimensional image corresponding to the three-dimensional conversion target region, such that the two-dimensional processed image is an image geometrically aligned with a position in the two-dimensional image corresponding to the three-dimensional conversion target region. The two-dimensional processed image referred to here is an example of a second image according to the technology disclosed herein.

For the sake of convenience, in the following explanation, the above-described two-dimensional processed image and the above-described three-dimensional processed image are both referred to as processed images unless it is necessary to differentiate between the two. Similarly, for the sake of convenience, in the following explanation a signal expressing the two-dimensional processed image is referred to as a two-dimensional processed image signal, and a signal expressing the three-dimensional processed image is referred to as a three-dimensional processed image signal. The two-dimensional processed image signal and the three-dimensional processed image signal are both referred to as processed image signals unless it is necessary to differentiate between the two. Moreover, in the following explanation, a two-dimensional image with a specified two-dimensional conversion target region is referred to as a specified target two-dimensional image, and a three-dimensional image with a specified three-dimensional conversion target region is referred to as a specified target three-dimensional image. The specified target two-dimensional image and the specified target three-dimensional image are both referred to as specified target images unless it is necessary to differentiate between the two.

The display control section 184A displays the two-dimensional image and the three-dimensional image alongside each other on the display 172A so as to enable visual comparison therebetween. In other words, the display control section 184A controls the display 172A so as to display the two-dimensional image and the three-dimensional image alongside each other on the display 172A so as to enable visual comparison therebetween.

On receipt of a change instruction to change the respective display sizes of the two-dimensional image and the three-dimensional image, the display control section 184A outputs to the display 172A a change instruction signal instructing a change in the display sizes according to the change instruction, thereby changing the respective display sizes of the two-dimensional image and the three-dimensional image on the display 172A. In other words, on receipt of a change instruction, the CPU 162A controls the display 172A so as to change the respective display sizes of the two-dimensional image and the three-dimensional image on the display 172A.

The display control section 184A displays the two-dimensional image, the three-dimensional image, and the OCT image alongside each other on the display 172A so as enable visual comparison therebetween. In other words, the display control section 184A controls the display 172A such that the two-dimensional image, the three-dimensional image, and the OCT image are displayed alongside each other on the display 172A so as to enable visual comparison therebetween.

The OCT image is an example of a tomographic image of the technology disclosed herein. An OCT image signal is a signal expressing an OCT image obtained by OCT imaging of a position in the examined eye 12 corresponding to a processed image. In cases in which the conversion target region is linear in shape, the OCT image is a two-dimensional OCT image, and in cases in which the conversion target region is planar in shape, the OCT image is a three-dimensional OCT image. The two-dimensional OCT image is a B-scan image obtained by what is referred to as a B-scan using the ophthalmic device 110, and the three-dimensional OCT image is for example a C-scan image obtained by what is referred to as a C-scan using the ophthalmic device 110.

On receipt of a magnified display instruction relating to the OCT image, the display control section 184A outputs a magnified display instruction signal instructing magnified display of the OCT image corresponding to the magnified display instruction to the display 172A, such that magnified display of the OCT image is performed on the display 172A. In other words, on receipt of a magnified display instruction relating to the OCT image, the display control section 184A controls the display 172A such that magnified display of the OCT image is performed on the display 172A. Note that the magnified display instruction relating to the OCT image is an instruction to magnify the display the OCT image on the display 172A.

The display control section 184A outputs a processed image signal to the display 172A such that the second image is displayed on the display 172A in a form in which a laser irradiation position mark is reflected at a position of the processed image. In other words, the display control section 184A controls the display 172A such that the processed image is displayed on the display 172A in a form reflecting the laser irradiation position mark. The laser irradiation position mark is generated by the image processing section 182A. The laser irradiation position mark is a pattern indicating a surgical laser irradiation position. A surgical laser is a laser employed in laser surgery on the examined eye 12.

The image processing section 182A detects vascular areas or avascular areas (AVA) in a specified target image. In the present exemplary embodiment, a vascular area is specified as a conversion target region based on detection results of the image processing section 182A. In the present exemplary embodiment, a vascular area is a region with neovascular blood vessels. An avascular area is a region of the fundus of the examined eye 12 where blood vessels are not present or where blood vessels are sparse. The vascular area or avascular area is detected by the image processing section 182A identifying a non-perfusion area (NPA) in the first image. A non-perfusion area is a region of the fundus where blood barely flows or does not flow at all, for example due to blockage of the retinal capillary bed.

Figure 23:
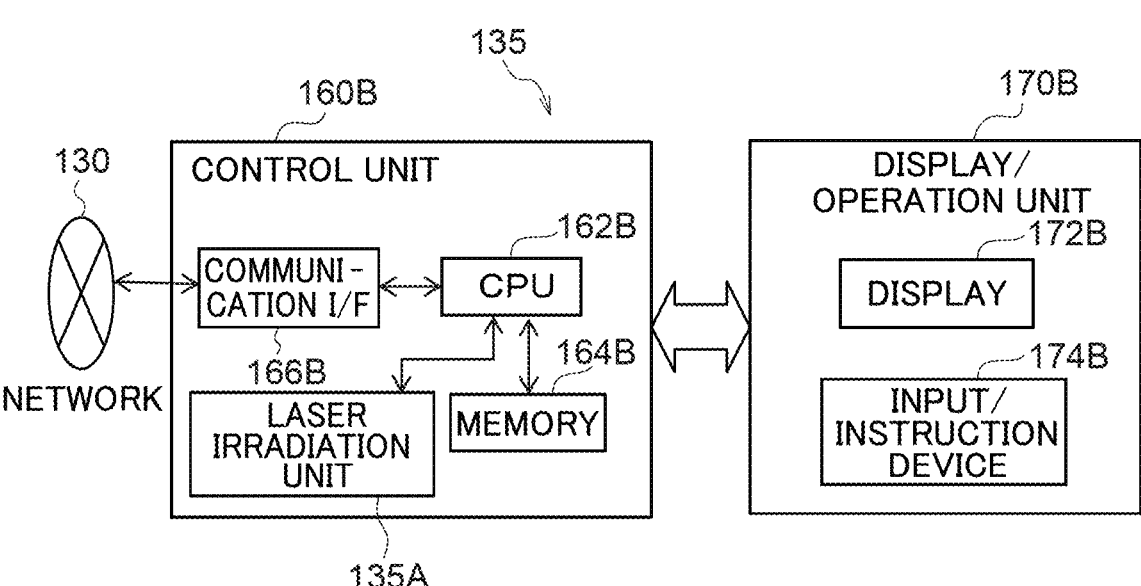
FIG. 23 is a block diagram illustrating configuration of a laser treatment device included in an ophthalmic system.

As illustrated in FIG. 23, the laser treatment device 135 differs from the management server 140 in the points that a control unit 160B is provided in place of the control unit 160, and a display/operation unit 170B is provided in place of the display/operation unit 170.

The control unit 160B differs from the control unit 160 illustrated in FIG. 5 in the point that a laser irradiation unit 135A is provided. The control unit 160B includes hardware resources that are basically the same as those of the control unit 160 illustrated in FIG. 5, with the exception of the inclusion of the laser irradiation unit 135A. In the control unit 160B, a CPU 162B corresponds to the CPU 162 illustrated in FIG. 5, a memory 164B corresponds to the memory 164 illustrated in FIG. 5, and a communication OF 166B corresponds to the communication OF 166 illustrated in FIG. 5. The laser irradiation unit 135A is coupled to the CPU 162B, and irradiates the fundus of the examined eye 12 with a surgical laser under the control of the CPU 162B.

The display/operation unit 170B includes hardware resources that are basically the same as those of the display/operation unit 170 illustrated in FIG. 5. In the display/operation unit 170B, a display 172B corresponds to the display 172 illustrated in FIG. 5, and an input/instruction device 174B corresponds to the input/instruction device 174 illustrated in FIG. 5.

Figure 7:
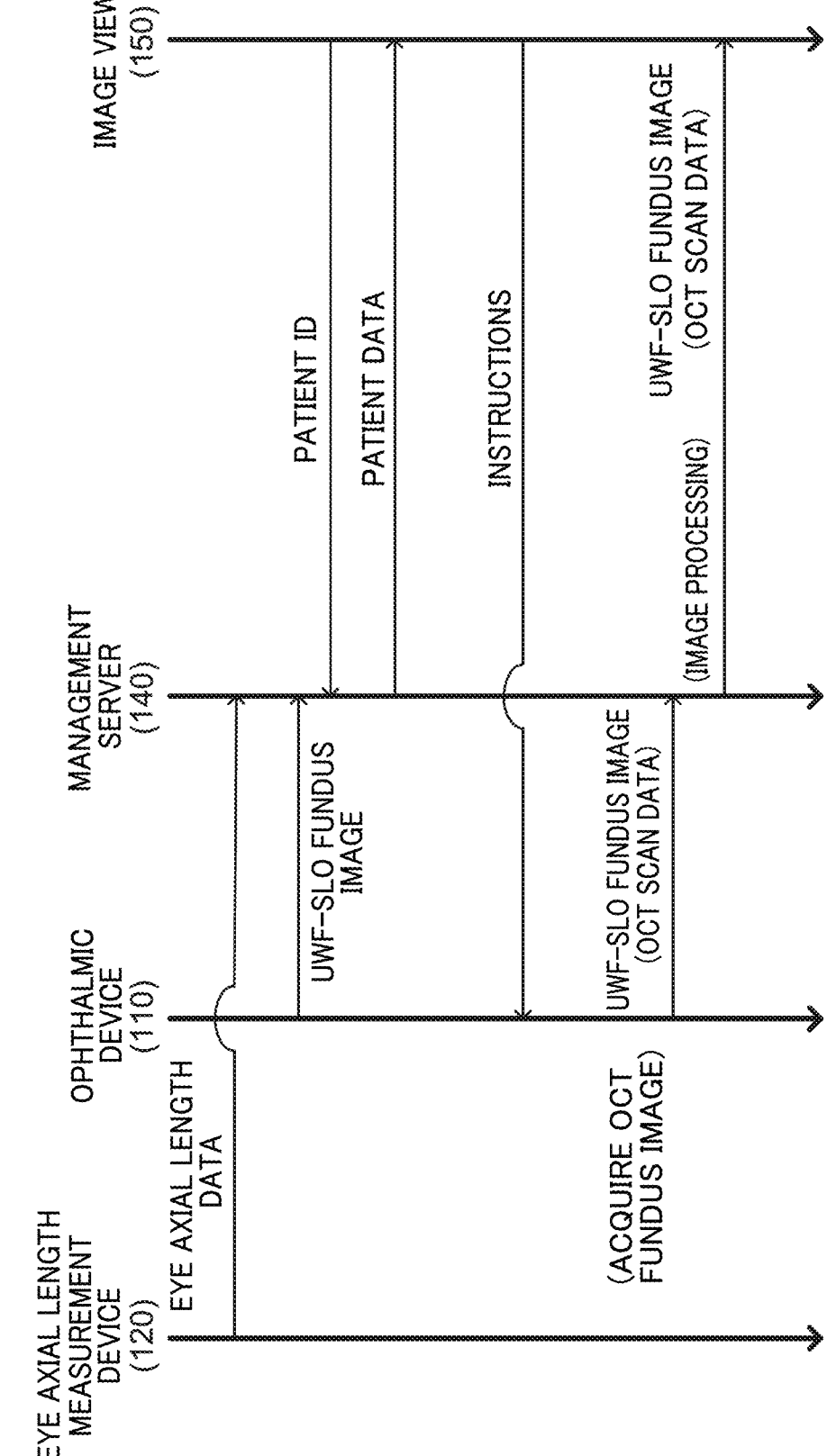
FIG. 7 is a sequencing diagram illustrating an example of various information exchanged between an eye axial length measurement device, an ophthalmic device, a management server, and an image viewer.

Explanation follows regarding overall operation of the ophthalmic system 100, with reference to FIG. 7.

First, the ophthalmic system 100 collects fundamental information relating to the examined eye 12 of the patient in order to make a diagnosis for the examined eye 12 of the patient. Specifically, first, the eye axial length measurement device 120 measures the eye axial length of the patient as instructed by an ophthalmologist. The eye axial length measurement device 120 transmits the measured eye axial length to the management server 140 together with the patient ID. The management server 140 stores the eye axial length in the memory 164 associated with the patient ID. The memory 164 is stored with personal information relating to the patient associated with the patient ID. The personal information includes the name, age, sex, visual acuity, and the like of the patient.

The examined eye 12 of the patient is imaged by the imaging device 14 of the ophthalmic device 110 to acquire a UWF-SLO fundus image. The ophthalmic device 110 transmits the acquired UWF-SLO fundus image to the management server 140 together with the patient ID. The management server 140 stores the UWF-SLO fundus image associated with the patient ID in the memory 164.

Figure 18:
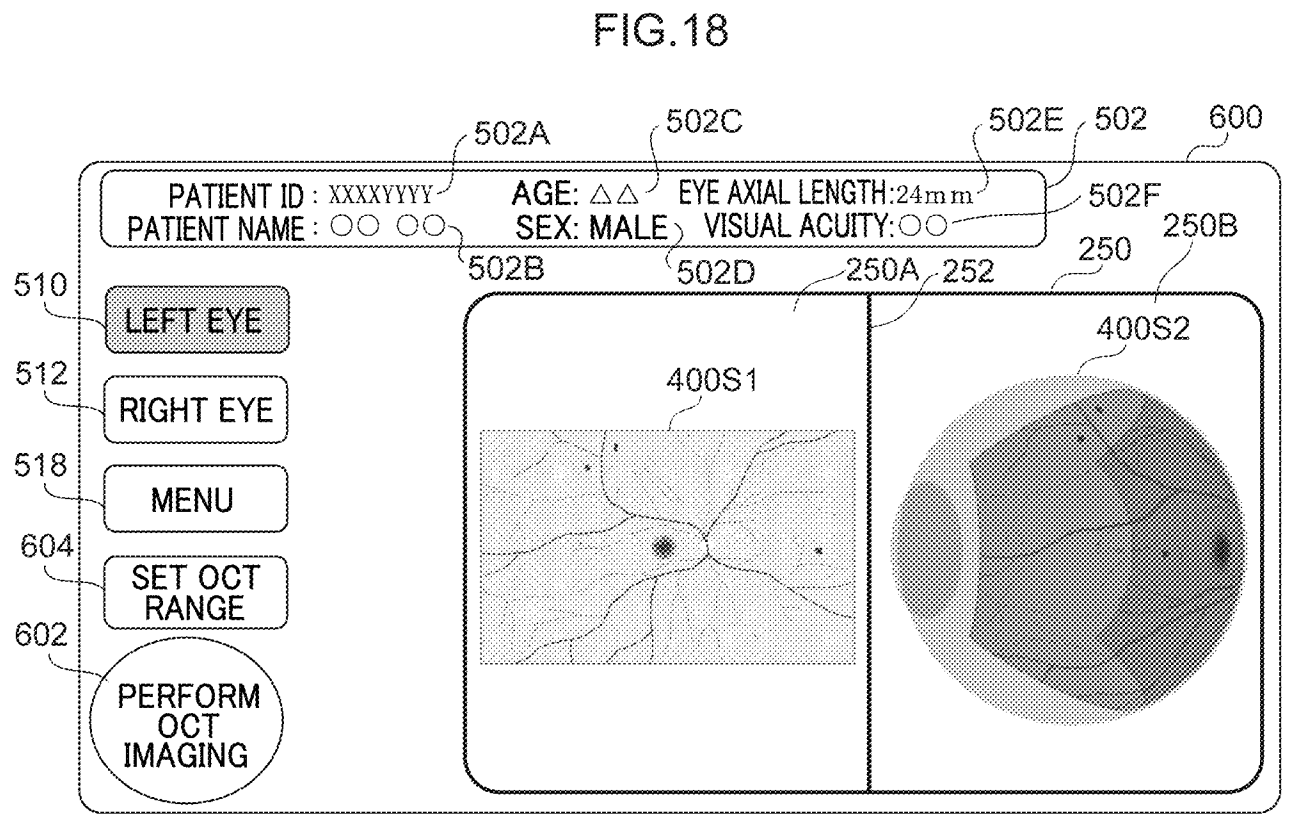

Detailed explanation follows regarding acquisition of the UWF-SLO fundus image using the ophthalmic device 110. First, an operator inputs the patient ID and the like using the input/display device 16E. The display control section 204 of the CPU 16A of the ophthalmic device 110 displays patient information and a non-illustrated menu screen for mode selection (a menu screen to select an SLO mode, an OCT mode, and various setting modes) on the display of the input/display device 16E. When the operator selects the SLO mode on the menu screen, the display control section 204 displays a viewer 2D/3D display screen 600, illustrated in FIG. 18, on the display 172 of the input/display device 16E. As illustrated in FIG. 18, the 2D/3D display screen 600 includes a patient information display field 502 and an examined eye check screen 250. The 2D/3D display screen 600 further includes a left eye button 510, a right eye button 512, a menu button 518, an OCT imaging button 602, and a set OCT range button 604.

The patient information display field 502 includes a patient ID display field 502A, a patient name display field 502B, an age display field 502C, a sex display field 502D, an eye axial length display field 502E, and a visual acuity display field 502F. The display control section 184A acquires data relating to the patient ID, the patient name, the patient age, the patient sex, the patient eye axial length, and the patient visual acuity from the management server 140. The display control section 184A displays information based on the acquired data in the patient ID display field 502A, the patient name display field 502B, the age display field 502C, the sex display field 502D, the eye axial length display field 502E, and the visual acuity display field 502F.

The left eye button 510 is a button used to specify the left eye as the eye of which the fundus is to be imaged. The right eye button 512 is a button used to specify the right eye as the eye of which the fundus is to be imaged. The OCT imaging button 602 is a button used to instruct OCT imaging. The set OCT range button 604 is a button used to set a desired imaging range for the OCT imaging. A UWF-SLO fundus image 400S acquired from the management server 140 is displayed on the examined eye check screen 250 of the 2D/3D display screen 600. In FIG. 18, a three-dimensional image 400S2 is displayed at a position alongside a UWF-SLO fundus image 400S1 on the examined eye check screen 250. Note that FIG. 18 illustrates a UWF-SLO fundus image 400S1 for the left eye and a three-dimensional image 400S2 for the left eye.

Figure 8:
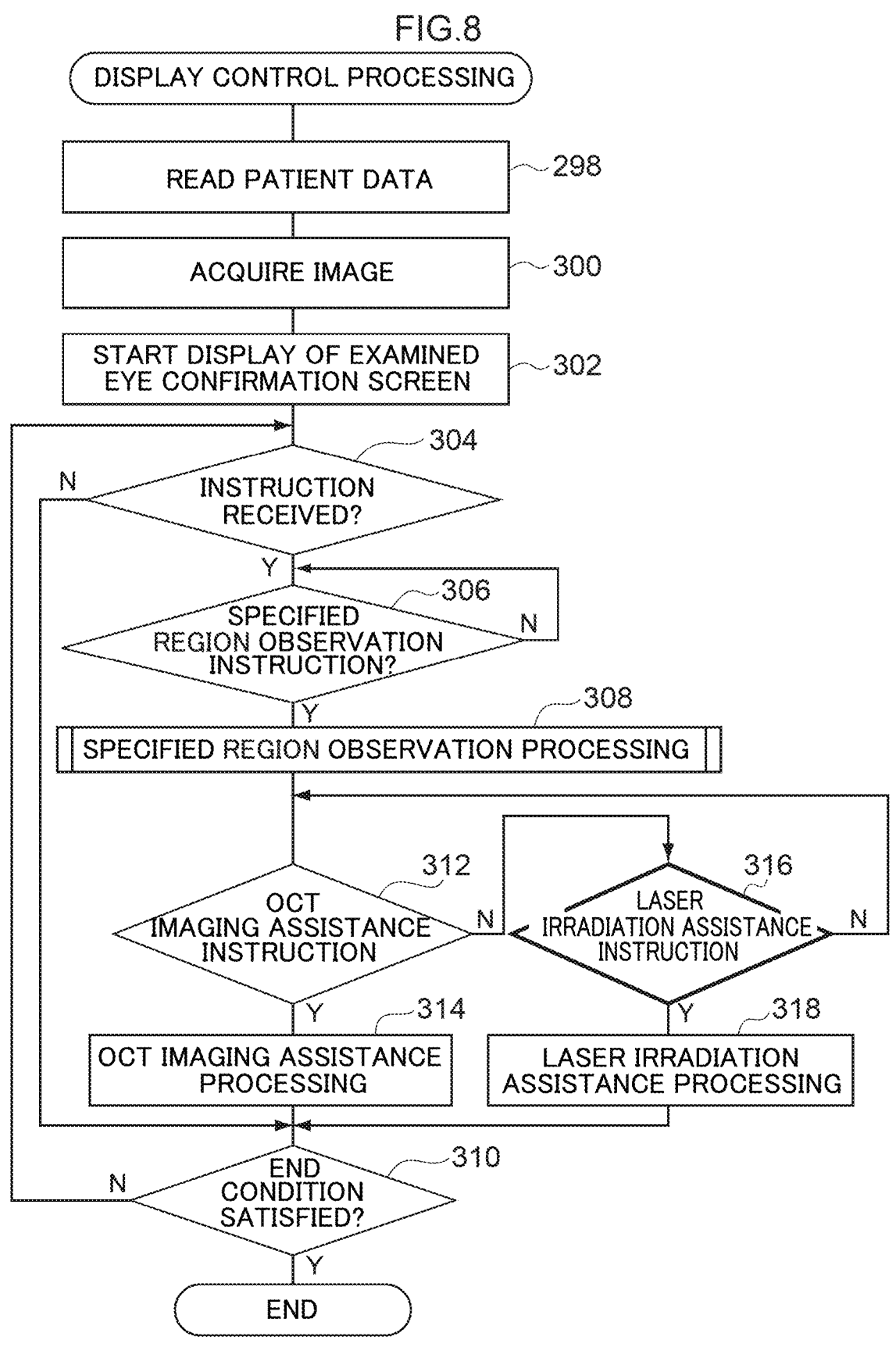
FIG. 8 is a flowchart illustrating a flow of display control processing.

Explanation follows regarding display control processing realized by the CPU 162A executing the control program when a display control processing execution start instruction has been received by the input/instruction device 174A of the image viewer 150, with reference to FIG. 8.

In the display control processing illustrated in FIG. 8, first, at step 298, the image processing section 182A reads the patient data from the memory 164A.

At the next step 300, the image processing section 182A acquires an SLO fundus image and a three-dimensional image from the patient data read from the memory 164A by executing the processing of step 298. The SLO fundus image acquired at step 300 is an example of the specified target two-dimensional image described previously, and the three-dimensional image acquired at step 300 is an example of the specified target three-dimensional image described previously.

At the next step 302, the display control section 184A displays the examined eye check screen 250, this being an example of a display screen according to the technology disclosed herein, on the display 172A based on the SLO fundus image and the three-dimensional image obtained by executing the processing of above step 300. The display control processing then transitions to step 304. Note that in the first exemplary embodiment, the examined eye check screen 250 is generated by the image processing section 182A, and the generated examined eye check screen 250 is displayed on the display 172A under the control of the display control section 184A.

Figure 9:
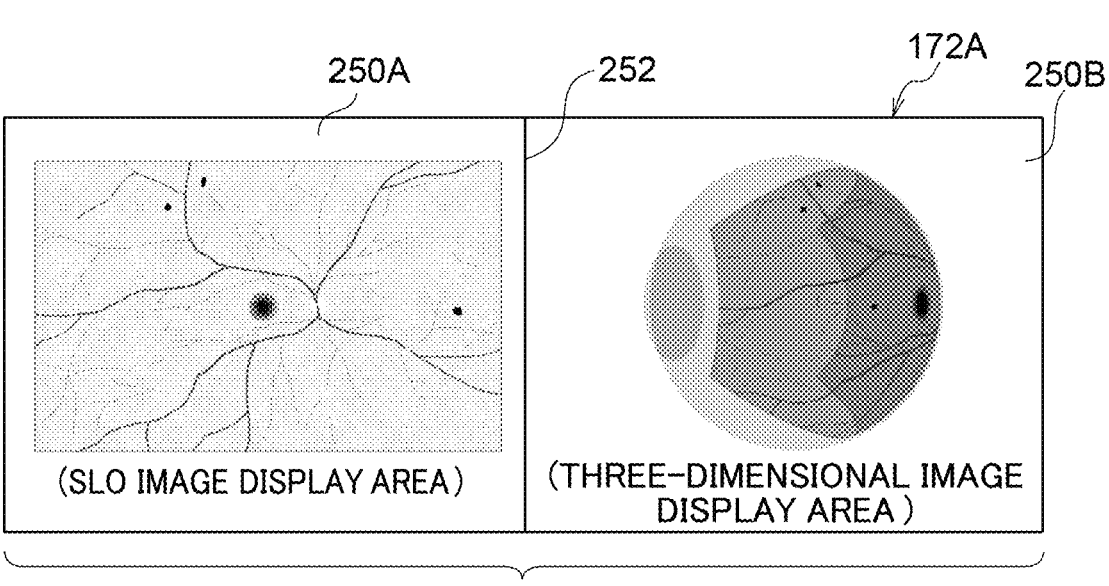
FIG. 9 is a diagram illustrating an SLO image display screen and a three-dimensional image display screen included on an examined eye check screen in a state displayed on a display of an image viewer.

As illustrated in FIG. 9, the examined eye check display screen 250 is broadly split into an SLO fundus image display area 250A, this being an example of a two-dimensional display region according to the technology disclosed herein, and a three-dimensional image display area 250B, this being an example of a three-dimensional display region according to the technology disclosed herein, on either side of a display screen dividing line 252.

The display screen dividing line 252 is a vertical line dividing the overall display 172A screen into two parts such that the SLO fundus image display screen 250A and the three-dimensional image display screen 250B are displayed alongside each other. Namely, one screen obtained by dividing the overall display 172A screen into two screens is the SLO fundus image display screen 250A, and the other screen is the three-dimensional image display screen 250B. In FIG. 9, the SLO fundus image is displayed on the SLO fundus image display screen 250A, and the three-dimensional image is displayed on the three-dimensional image display screen 250B.

The size of the SLO fundus image display screen 250A and the size of the three-dimensional image display screen 250B can be changed. The size of the SLO fundus image display screen 250A and the size of the three-dimensional image display screen 250B can be changed by the display control section 184A by moving the display screen dividing line 252 in a left-right direction.

In the present exemplary embodiment, the image processing section 182A converts two-dimensional images (also referred to hereafter as 2D images) into three-dimensional images (also referred to hereafter as 3D images), and also converts 3D images into 2D images. Namely, the image processing section 182A converts 2D image data expressing a 2D image into 3D image data expressing a 3D image based on an eyeball model, and generates 2D image data from 3D image data by the reverse of this conversion. Note that the method for converting a two-dimensional image into a three-dimensional image may employ the technology disclosed in U.S. Pat. No. 8,422,750.

At step 304, the processing section 186A determines whether or not one instruction out of three predetermined instructions has been received by the input/instruction device 174A. The three predetermined instructions are a specified region observation instruction, an OCT imaging assistance instruction, and a laser irradiation assistance instruction. The specified region observation instruction is an instruction to start execution of specified region observation processing, described later. The OCT imaging assistance instruction is an instruction to start execution of OCT imaging assistance processing, described later. The laser irradiation assistance instruction is an instruction to start execution of laser irradiation assistance processing, described later.

In cases in which no one instruction out of the three predetermined instructions has been received by the input/instruction device 174A, the determination of step 304 is negative, and the display control processing transitions to step 310. In cases in which one instruction out of the three predetermined instructions has been received by the input/instruction device 174A, the determination of step 304 is affirmative, and the display control processing transitions to step 306.

At step 306, the processing section 186A determines whether or not the instruction received by the input/instruction device 174A is a specified region observation instruction. At step 306, in cases in which the instruction received by the input/instruction device 174A is not a specified region observation instruction, determination is negative, and the determination of step 306 is performed again. At step 306, in cases in which the instruction received by the input/instruction device 174A is a specified region observation instruction, determination is affirmative, and the display control processing transitions to step 308.

Figure 10:
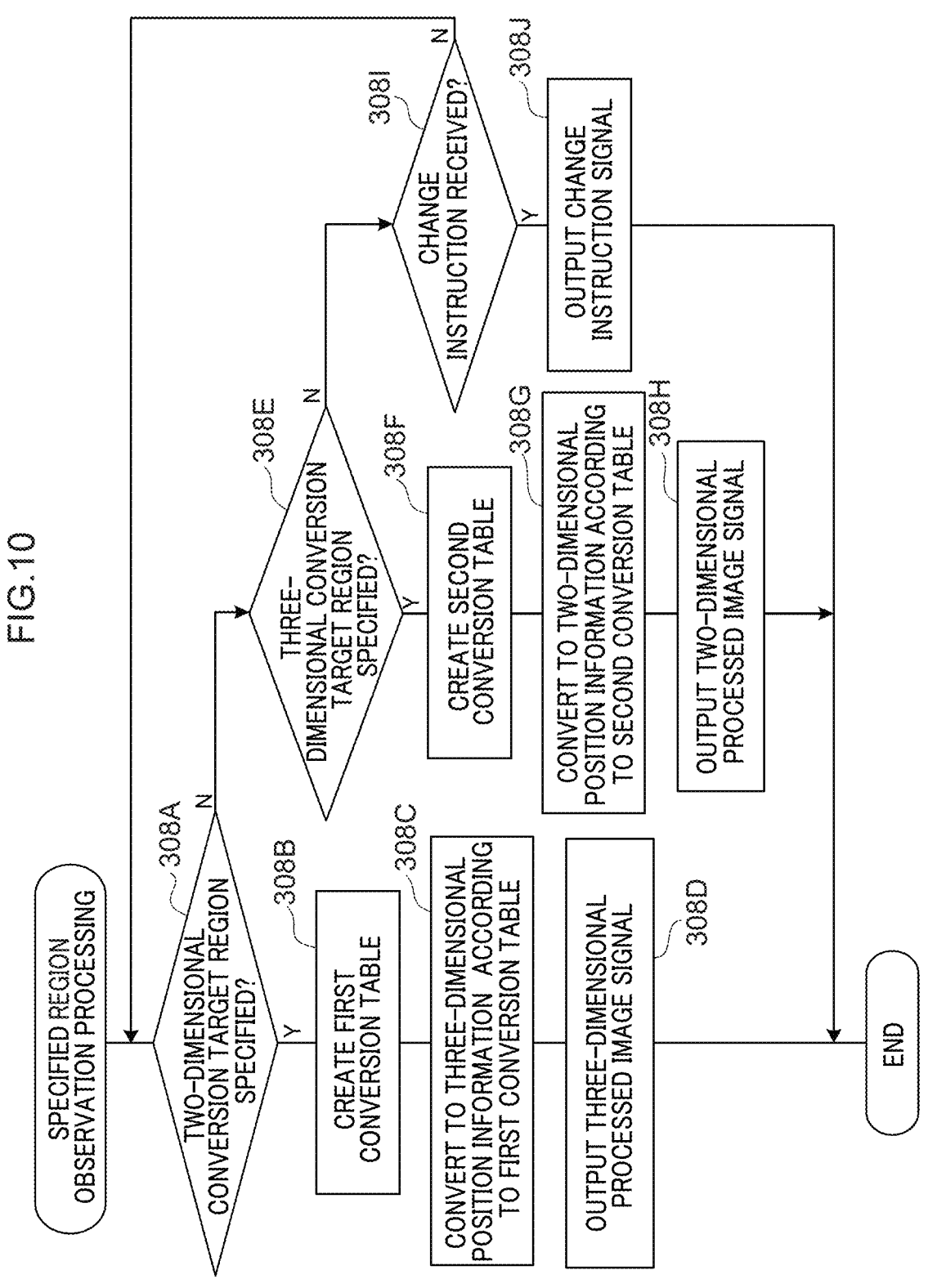
FIG. 10 is a flowchart illustrating a flow of specified region observation processing included in display control processing.

At step 308, the CPU 162A executes the specified region observation processing illustrated in FIG. 10, after which processing transitions to step 310.

In the specified region observation processing illustrated in FIG. 10, first at step 308A, the processing section 186A determines whether or not a two-dimensional conversion target region has been specified in the SLO fundus image being displayed on the SLO fundus image display screen 250A. The two-dimensional conversion target region is set in response to instructions received by the input/instruction device 174A.

Although an example is given in which the two-dimensional conversion target region is set in response to instructions received by the input/instruction device 174A, the technology disclosed herein is not limited thereto. Configuration may be made such that the image processing section 182A detects a vascular area or an avascular area in the SLO fundus image and the vascular area is specified as the two-dimensional conversion target region based on the detection result of the image processing section 182A. Alternatively, configuration may be made such that the image processing section 182A detects a neovascular area and the detected neovascular area is specified as the two-dimensional conversion target region.

Figure 11A:
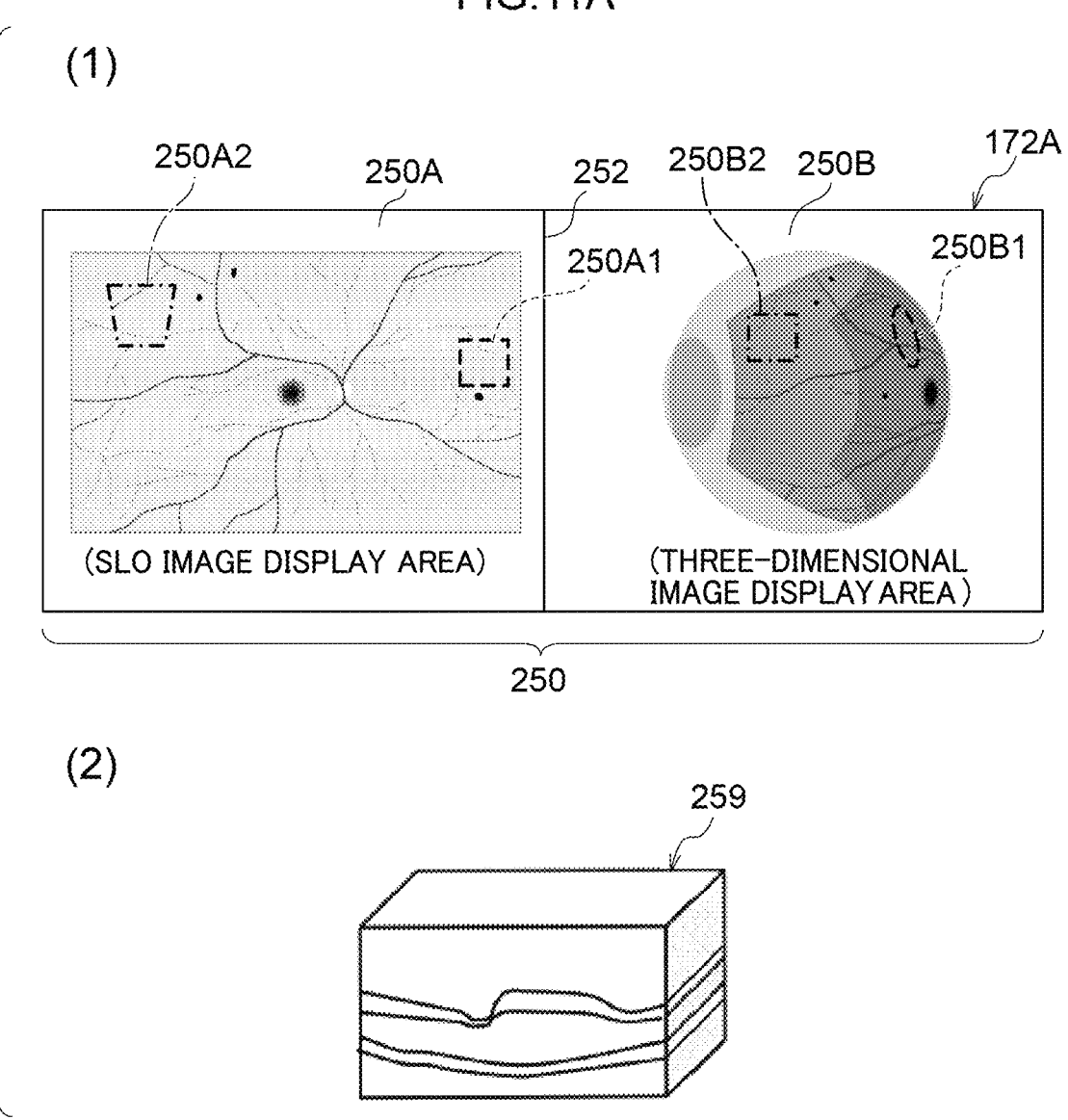
FIG. 11A is a schematic diagram illustrating display contents of an examined eye check screen in a state displayed on a display of an image viewer, where (1) is a schematic diagram illustrating display contents of an SLO image display screen and a three-dimensional image display screen, and (2) is a schematic diagram illustrating a three-dimensional OCT image displayed on the examined eye check screen.

FIG. 11A (1) illustrates an example in which a two-dimensional conversion target region has been specified and a two-dimensional conversion target region image 250A1 indicating the specified two-dimensional conversion target region has been specified. As illustrated in FIG. 11A (1), when the two-dimensional conversion target region image 250A1 is specified in the SLO fundus image, the two-dimensional conversion target region image 250A1 is displayed overlaid on the SLO fundus image using an emphatic display enabling the two-dimensional conversion target region image 250A1 to be differentiated from other regions of the image. In FIG. 11A (1), the outline of the two-dimensional conversion target region image 250A1 is displayed by dashed lines in order to realize the emphatic display that enables the two-dimensional conversion target region image 250A1 to be differentiated from other regions of the image.

In cases in which a two-dimensional conversion target region has been specified in the SLO fundus image being displayed on the SLO fundus image display screen 250A, the determination of step 308A is affirmative and the specified region observation processing transitions to step 308B. In cases in which a two-dimensional conversion target region has not been specified in the SLO fundus image being displayed on the SLO fundus image display screen 250A, the determination of step 308A is negative and the specified region observation processing transitions to step 308E.

At step 308B, the image processing section 182A creates a first conversion table, and then the specified region observation processing transitions to step 308C. The first conversion table is a table expressing correspondence relationships between two-dimensional position information relating to each of the pixels in the two-dimensional conversion target region image specified by the processing of step 308A, and three-dimensional position information relating to each of the corresponding pixels in the three-dimensional image. The first conversion table is created based on position correspondence information included in the patient data by extracting position correspondence information corresponding to each of the pixels in the two-dimensional conversion target region image specified by the processing of step 308A.

At step 308C, the image processing section 182A converts the two-dimensional position information relating to each of the pixels in the two-dimensional conversion target region image specified by the processing of step 308A into three-dimensional position information according to the first conversion table created by the processing of step 308B. The specified region observation processing then transitions to step S308D.

At step 308D, the display control section 184A outputs a three-dimensional processed image signal expressing a three-dimensional processed image to the display 172A, after which the specified region observation processing ends. Note that the three-dimensional processed image signal is generated by the image processing section 182A. An example of the three-dimensional processed image signal is a signal expressing a three-dimensional image generated by converting the two-dimensional conversion target region image 250A1 into three dimensions.

In other words, the three-dimensional processed image signal is a signal expressing the three-dimensional processed image obtained by geometrically aligning the two-dimensional conversion target region image representing the two-dimensional conversion target region specified at step 308A with a corresponding position in the three-dimensional image acquired at step 300, and converting the two-dimensional conversion target region image. The three-dimensional processed image is an image formed by respective pixels of the three-dimensional image being displayed on the three-dimensional image display screen 250B, these pixels being identified from the three-dimensional position information obtained by executing the processing of step 308C.

When the processing of step 308D is executed and the three-dimensional processed image signal is output to the display 172A by the display control section 184A, the display 172A displays the three-dimensional image in a form reflecting the three-dimensional processed image. In other words, the CPU 162A executes the processing of step 308D to control the display 172A so as to display the three-dimensional image in a form reflecting the three-dimensional processed image on the display 172A.

Namely, in a case in which a two-dimensional conversion target region has been specified in the SLO fundus image, an image, resulting from aligning the two-dimensional conversion target region image with a corresponding position in the three-dimensional image and converting the two-dimensional conversion target image, is displayed overlaid on the three-dimensional image.

In FIG. 11A (1), the outline of a three-dimensional processed image 250B1 identified by the three-dimensional position information corresponding to the two-dimensional image information relating to each of the pixels in the two-dimensional conversion target region image 250A1 is displayed by dashed lines. By displaying the outline of the three-dimensional processed image 250B1 with dashed lines in this manner, the three-dimensional processed image 250B1 is displayed in the three-dimensional image such that the three-dimensional processed image 250B1 can be differentiated from other regions. In other words, the three-dimensional processed image 250B1 obtained by performing geometric conversion on the two-dimensional conversion target region image 250A1 is displayed in the three-dimensional image such that the three-dimensional processed image 250B1 can be differentiated from other regions.

In cases in which the two-dimensional conversion target region image 250A1 has a rectangular shape as illustrated in FIG. 11A (1), OCT volume data is acquired by the ophthalmic device 110. The OCT volume data is acquired by the image processing section 182A of the image viewer 150 from the ophthalmic device 110 via the management server 140. The OCT volume data acquired by the image processing section 182A is subjected to various image processing by the image processing section 182A. The OCT volume data that has been subjected to various image processing is output to the display 172A by the display control section 184A, and a 3D image of the retina is displayed on the display 172A. As illustrated in FIG. 11A (2), the OCT volume data referred to here is a three-dimensional OCT image 259, this being what is referred to as a C-scan image.

Note that although an example of a case in which the two-dimensional conversion target region image 250A1 has a rectangular shape has been given for ease of explanation, the technology disclosed herein is not limited thereto. Configuration may be such that a three-dimensional OCT image is acquired by the ophthalmic device 110 and this three-dimensional OCT image is displayed on the display 172A in cases in which a planar region with a trapezoid shape, a circular shape, or the like is specified in the SLO fundus image.

By executing the processing of steps 308A to 308D, the two-dimensional conversion target region image is converted aligned with the geometric characteristics of the corresponding position in the three-dimensional image, and the mutually related two-dimensional conversion target region image and three-dimensional processed image are displayed alongside each other on the display 172A so as to enable visual comparison therebetween.

Figure 11B:
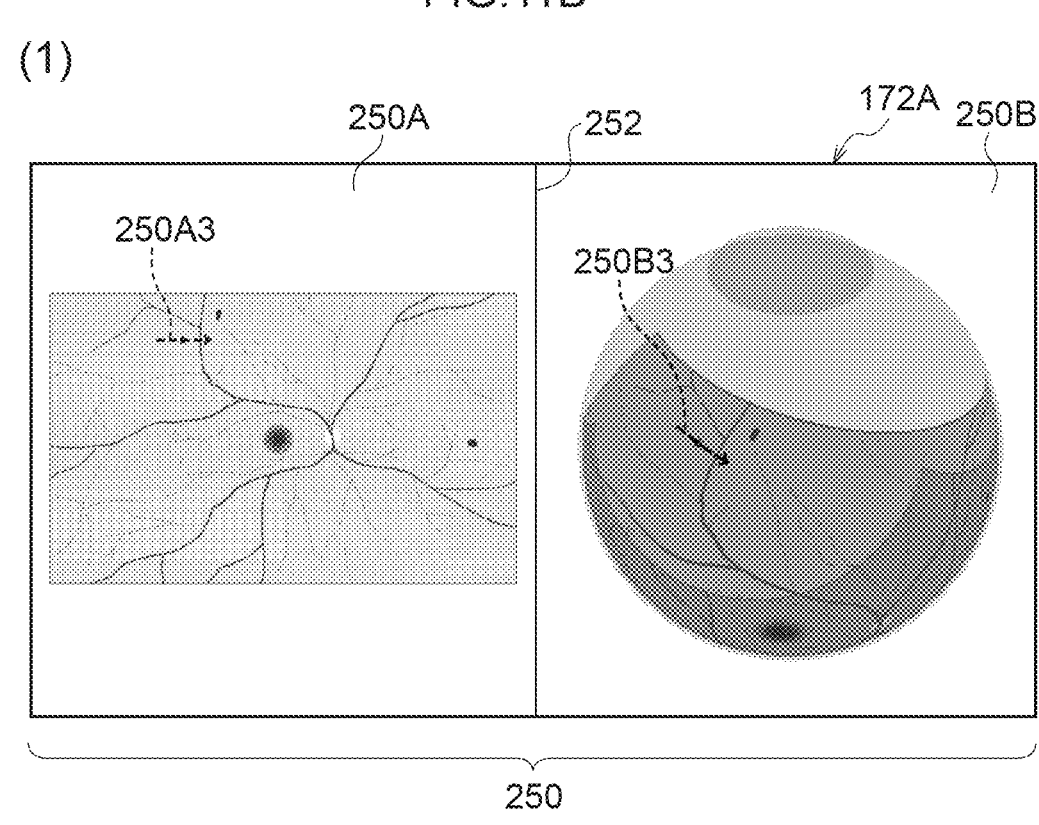
FIG. 11B is a schematic diagram illustrating display contents of an examined eye check screen in a state displayed on a display of an image viewer, where (1) is a schematic diagram illustrating display contents of an SLO image display screen and a three-dimensional image display screen, and (2) is a schematic diagram illustrating a tomographic image displayed on the examined eye check screen.
Figure 11B:
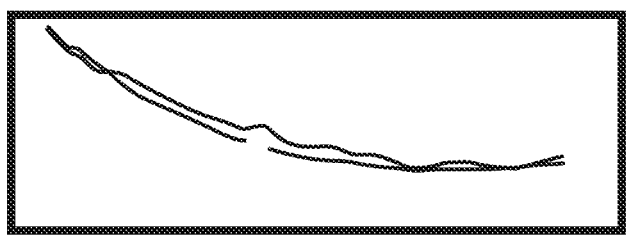
Figure 11C:
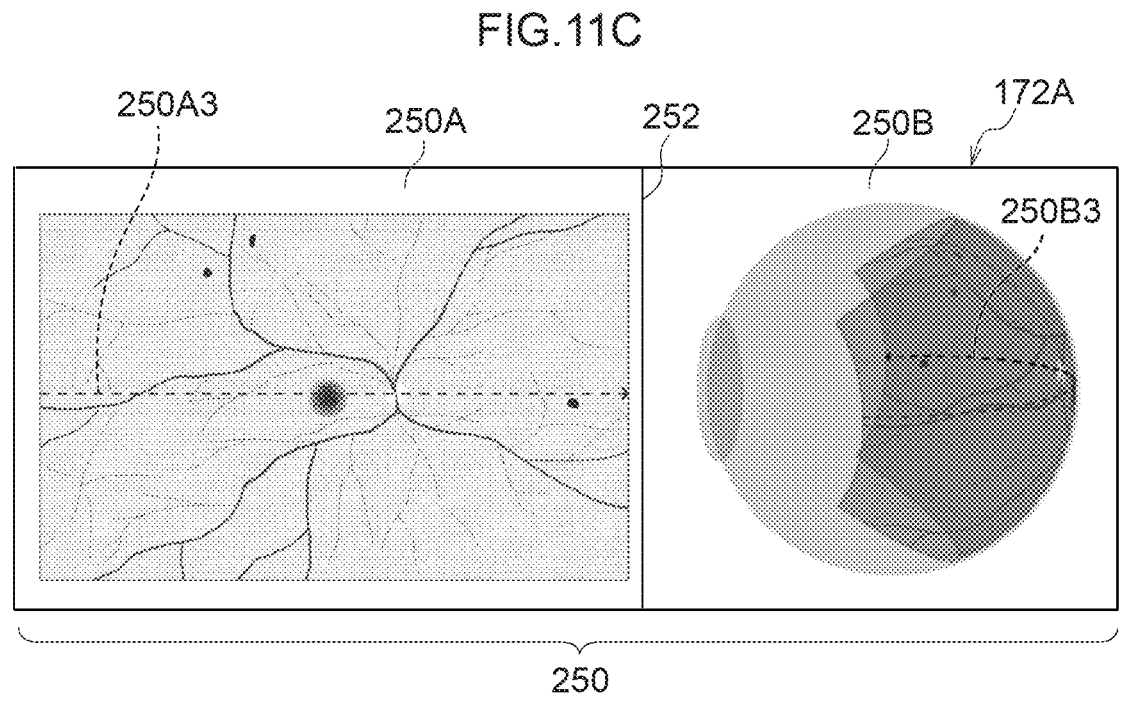

A linear two-dimensional conversion target region image 250A3 illustrated in FIG. 11B (1) is an example of a two-dimensional conversion target region image representing a two-dimensional conversion target region specified by a user. In FIG. 11B (1), a linear three-dimensional processed image 250B3 corresponding to the two-dimensional conversion target region image 250A3 is displayed on the three-dimensional image display screen 250B. FIG. 11C illustrates a two-dimensional conversion target region image 250A3 with a longer line segment than in the example illustrated in FIG. 11B (1), and a three-dimensional processed image 250B3 with a longer line segment than in the example illustrated in FIG. 11B (1).

When a linear two-dimensional conversion target region is specified by a user, a two-dimensional OCT image, this being what is referred to as a B-scan image, is acquired by the ophthalmic device 110 based on the two-dimensional conversion target region image 250A3 representing the specified linear two-dimensional conversion target region. The two-dimensional OCT image is then acquired from the ophthalmic device 110 by the image processing section 162 of the image viewer 150 via the management server 140. The two-dimensional OCT image acquired by the image processing section 162 of the image viewer 150 is subjected to various image processing by the image processing section 162 of the image viewer 150. The two-dimensional OCT image that has been subjected to the various image processing is then output to the display 172A by the display control section 184A, and a tomographic image of the retina is displayed on the display 172A as illustrated in FIG. 11B (2).

When an instruction from the user using the input/instruction device 174A of the image viewer 150 is received in a state in which a three-dimensional image is being displayed on the three-dimensional image display screen 250B illustrated in FIG. 11B (1), a pull-down menu is displayed on the display 172A. The pull-down menu includes a "rotate" menu option, and when the user selects the "rotate" menu option using the input/instruction device 174A, the three-dimensional image can be rotated by performing a dragging operation with a mouse included in the input/instruction device 174. Note that rotation of the three-dimensional image in the three-dimensional image display screen 250B is realized by the display control section 184A controlling the display 172A in response to instructions received through the input/instruction device 174A.

Figure 14A:
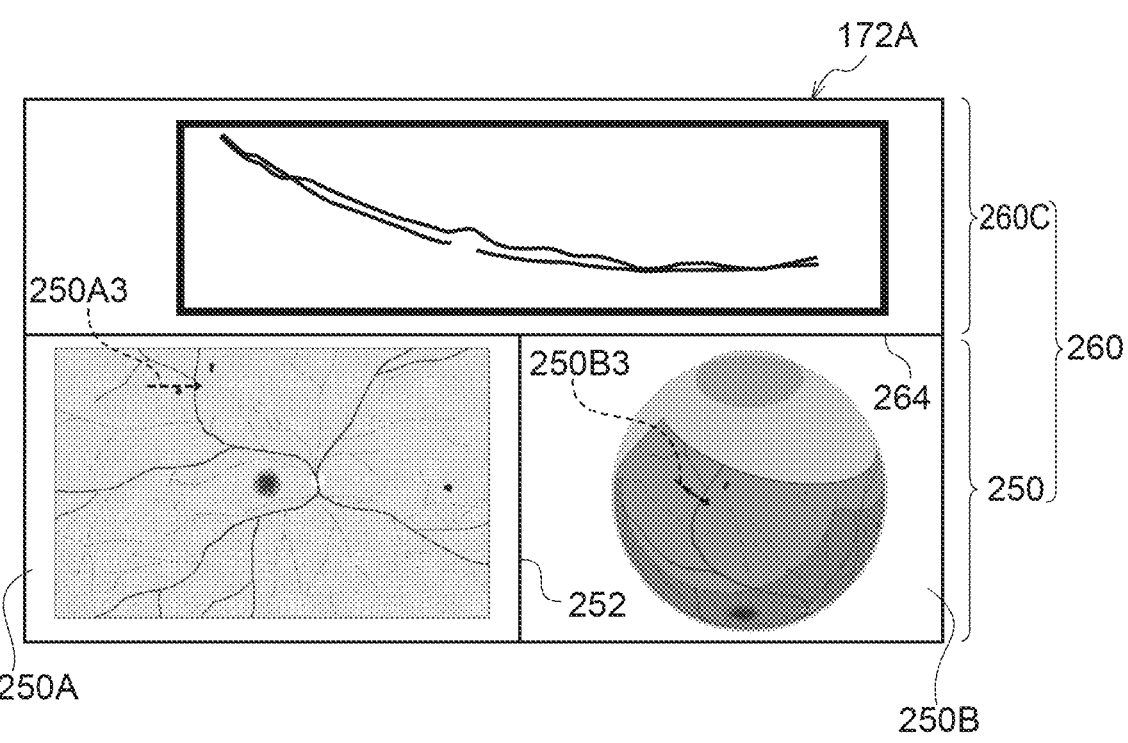
FIG. 14A is a diagram illustrating an examined eye check screen in a state displayed on a display of an image viewer, when an SLO fundus image display screen, a three-dimensional image display screen, and an OCT image display screen are displayed.

The two-dimensional OCT image may be displayed alongside the SLO fundus image and the three-dimensional image. FIG. 14A illustrates an examined eye check screen 260. The examined eye check screen 260 is a screen combining the examined eye check screen 250 described above and an OCT image display screen 260C. Namely, the examined eye check screen 260 is broadly split into the SLO fundus image display screen 250A, the three-dimensional image display screen 250B, and the OCT image display screen 260C. In FIG. 14A, the overall display 172 screen is divided into three by the display screen dividing line 252, this being a vertical dividing line, and a horizontal dividing line 264.

In FIG. 14A, the SLO fundus image display screen 250A and the three-dimensional image display screen 250B are disposed on either horizontal direction side of the display screen dividing line 252. The SLO fundus image is displayed on the SLO fundus image display screen 250, and the three-dimensional image is displayed on the three-dimensional image display screen 250B. In FIG. 14A, the examined eye check screen 250 is displayed at the vertical direction lower side of the horizontal dividing line 264, and the OCT image display screen 260C is displayed at the vertical direction upper side of the horizontal dividing line 264. The most recent B-scan image, namely an OCT image expressed by the most recent OCT image signal to have been acquired by the image processing section 162 of the image viewer 150, is displayed on the OCT image display screen 260C.

Note that although in FIG. 14A a B-scan image is displayed on the OCT image display screen 260C, the technology disclosed herein is not limited thereto. As illustrated in FIG. 11A (1), in cases in which the two-dimensional conversion target region image 250A1 or a three-dimensional conversion target region image 250B2 is planar, instead of a B-scan image, the three-dimensional OCT image 259 (see FIG. 11A (2)) may be displayed on the OCT image display screen 260C as a three-dimensional retinal image corresponding to the two-dimensional conversion target region image 250A1 or the three-dimensional conversion target region image 250B2.

Figure 14B:
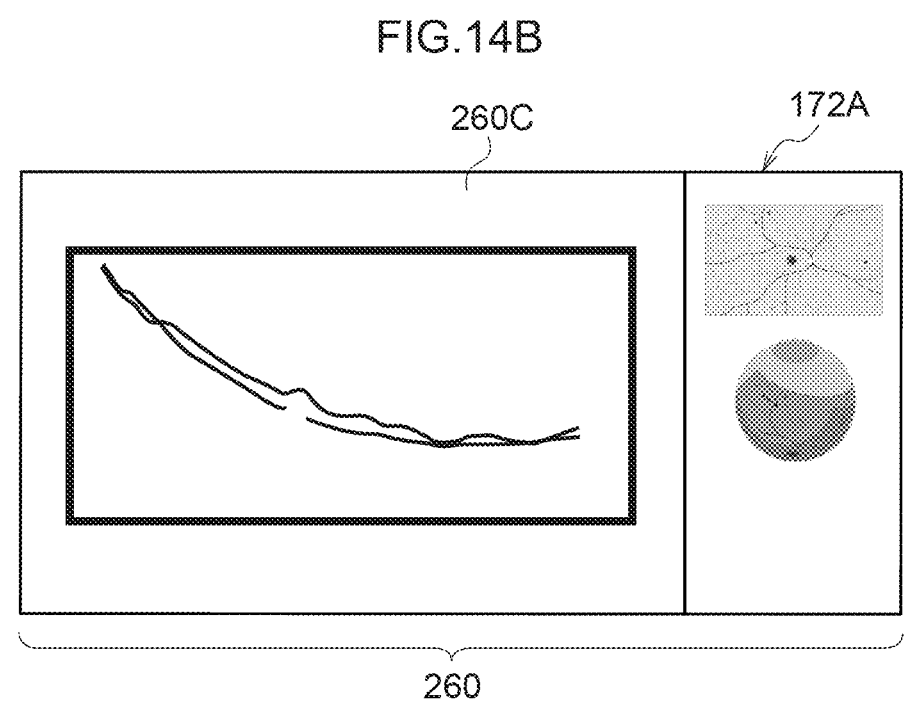
FIG. 14B is a diagram illustrating an examined eye check screen in a state displayed on a display of an image viewer, in a state in which an OCT image display screen has been magnified on the examined eye check screen.

Alternatively, the display control section 184A may display a magnified OCT image on the display 172A in response to an instruction received by the input/instruction device 174 of the image viewer 150. Note that in FIG. 14B, a magnified OCT image is displayed by magnifying the OCT image display screen 260C.

In this manner, the image viewer 150 displays an OCT image on the display 172A so as to enable a doctor to check an OCT image of a location deemed to be of concern in the examined eye 12 and to perform an examination of the examined eye 12. Moreover, the image viewer 150 displays the SLO fundus image, the three-dimensional image, and the OCT image side-by-side on the display 172A so as to enable visual comparison therebetween, thereby enabling the doctor to easily identify which part of the examined eye 12 is being displayed in the OCT image.

Figure 15A:
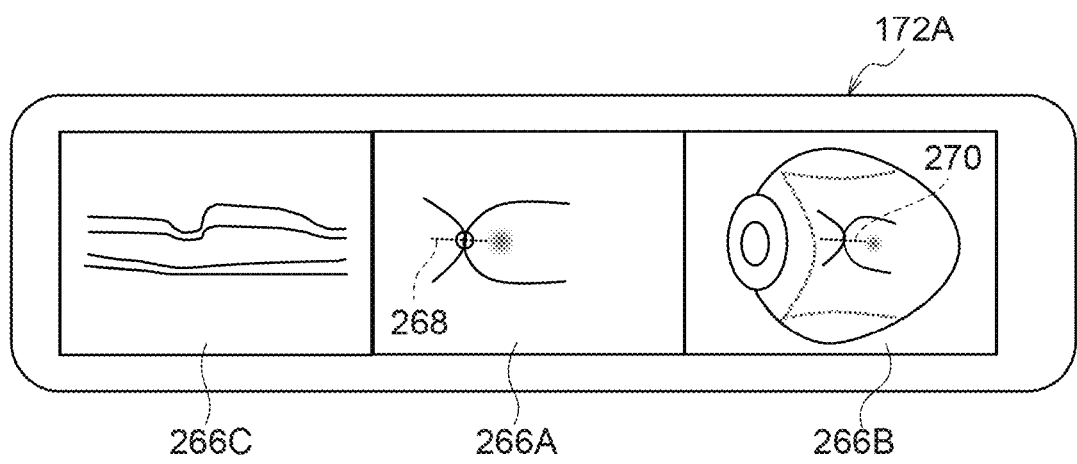
FIG. 15A is a screen diagram illustrating an examined eye check screen in a state displayed on a display of an image viewer, in a state in which a linear two-dimensional conversion target region is displayed as an OCT B-scan position.

FIG. 15A illustrates another example in which the SLO fundus image, the three-dimensional image, and the OCT image are displayed alongside each other on the display 172A. In FIG. 15A, an SLO fundus image display screen 266A, a three-dimensional image display screen 266B, and an OCT image display screen 266C are displayed side-by-side on the display 172A along the horizontal direction. Moreover, in FIG. 15A, the SLO fundus image display screen 266A is displayed at a central portion of the display 172A, and the OCT image display screen 266C and the three-dimensional image display screen 266B are displayed on either side of the SLO fundus image display screen 266A.

The SLO fundus image is displayed on the SLO fundus image display screen 266A, and a linear two-dimensional conversion target region image 268 is displayed in the SLO fundus image as an OCT B-scan position. The three-dimensional image is displayed on the three-dimensional image display screen 266B, and a three-dimensional processed image 270 corresponding to the two-dimensional conversion target region image 268 is displayed in the three-dimensional image. A two-dimensional OCT image, this being a B-scan image of a position of the examined eye 12 corresponding to the three-dimensional processed image 270, is displayed on the OCT image display screen 266C.

Figure 15B:
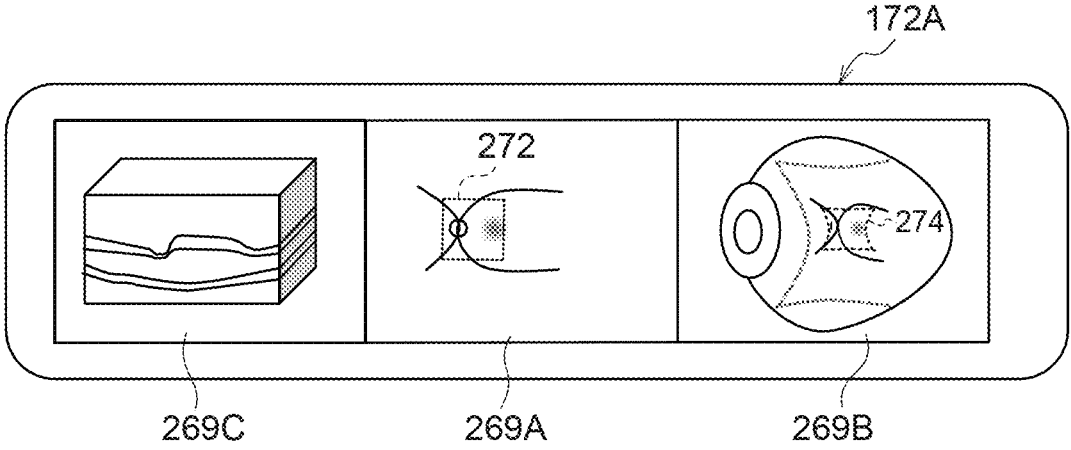
FIG. 15B is a screen diagram illustrating an examined eye check screen in a state displayed on a display of an image viewer, in a state in which a rectangular shaped two-dimensional conversion target region is displayed as an OCT C-scan position.

Moreover, in FIG. 15B, a SLO fundus image display screen 269A, a three-dimensional image display screen 269B, and an OCT image display screen 269C are displayed side-by-side on the display 172A along the horizontal direction. Moreover, in FIG. 15B, the SLO fundus image display screen 269A is displayed at a central portion of the display 172A, and the OCT image display screen 269C and the three-dimensional image display screen 269B are displayed on either side of the SLO fundus image display screen 269A.

The SLO fundus image is displayed on the SLO fundus image display screen 269A, and a rectangular shaped two-dimensional conversion target region image 272 is displayed in the SLO fundus image as an OCT C-scan position. The three-dimensional image is displayed on the three-dimensional image display screen 269B, and a planar three-dimensional processed image 274 corresponding to the two-dimensional conversion target region image 268 is displayed in the three-dimensional image. A three-dimensional OCT image, this being a C-scan image of a position of the examined eye 12 corresponding to the three-dimensional processed image 274, is displayed on the OCT image display screen 266C.

At step 308E, the processing section 186A determines whether or not a three-dimensional conversion target region has been specified in the three-dimensional image displayed on the three-dimensional image display screen 250B. The three-dimensional conversion target region is set in response to instructions received by the input/instruction device 174A.

Although an example is given here of a form in which the three-dimensional conversion target region is set in response to instructions received by the input/instruction device 174A, the technology disclosed herein is not limited thereto. Configuration may be made such that the image processing section 182A detects a vascular area or an avascular area in the SLO fundus image and a vascular area is specified as the three-dimensional conversion target region based on the detection result of the image processing section 182A. Alternatively, configuration may be made such that the image processing section 182A detects a neovascular area and the detected neovascular area is specified as the three-dimensional conversion target region.

FIG. 11A (1) illustrates an example in which a three-dimensional conversion target region has been specified and the three-dimensional conversion target region image 250B2 indicating the specified three-dimensional conversion target region has been specified. As illustrated in FIG. 11A (1), when the three-dimensional conversion target region 250B2 is specified in the three-dimensional image, the three-dimensional conversion target region image 250B2 is displayed overlaid on the three-dimensional image using an emphatic display enabling the three-dimensional conversion target region image 250B2 to be differentiated from other image regions. In FIG. 11A (1), the outline of the three-dimensional conversion target region 250B2 is displayed by single-dotted dashed lines in order to realize the emphatic display that enables the three-dimensional conversion target region image 250B2 to be differentiated from other image regions.

In cases in which a three-dimensional conversion target region has been specified in the three-dimensional image being displayed on the three-dimensional image display screen 250B, the determination of step 308E is affirmative and the specified region observation processing transitions to step 308F. In cases in which a three-dimensional conversion target region has not been specified in the three-dimensional image being displayed on the three-dimensional image display screen 250B, the determination of step 308E is negative and the specified region observation processing transitions to step 308I.

In cases in which the three-dimensional conversion target region 250B2 has a rectangular shape as illustrated in FIG. 11A (1), OCT volume data is acquired by the ophthalmic device 110. The OCT volume data is acquired by the image processing section 182A of the image viewer 150 from the ophthalmic device 110 via the management server 140. The OCT volume data acquired by the image processing section 162 of the image viewer 150 is subjected to various image processing by the image processing section 162 of the image viewer 150. The OCT volume data that has been subjected to the various image processing is output to the display 172A by the display control section 184A, and a 3D image of the retina is displayed on the display 172A as illustrated in FIG. 11A (2).

Note that although an example of a case in which the three-dimensional conversion target region image 250B2 has a rectangular shape has been given for ease of explanation, the technology disclosed herein is not limited thereto. Configuration may be such that a three-dimensional OCT image is acquired by the ophthalmic device 110 and this three-dimensional OCT image is displayed on the display 172A in cases in which a planar region with a trapezoid shape, a circular shape, or the like is specified in the SLO fundus image.

At step 308F, the image processing section 182A creates a second conversion table, and then the specified region observation processing transitions to step 308G. The second conversion table is a table expressing correspondence relationships between three-dimensional position information relating to each of the pixels in the three-dimensional conversion target region image specified by the processing of step 308E, and two-dimensional position information relating to each of the corresponding pixels in the SLO fundus image. The second conversion table is created based on position correspondence information included in the patient data by extracting position correspondence information corresponding to each of the pixels in the three-dimensional conversion target region image specified by the processing of step 308E.

At step 308G, the image processing section 182A converts the three-dimensional position information relating to each of the pixels in the three-dimensional conversion target region image specified by the processing of step 308E into two-dimensional position information according to the second conversion table created by the processing of step 308F. The specified region observation processing then transitions to step 308H.

At step 308H, the display control section 184A outputs a two-dimensional processed image signal expressing a two-dimensional processed image to the display 172A, after which the specified region observation processing ends. Note that the two-dimensional processed image signal is generated by the image processing section 182A. An example of the two-dimensional processed image signal is a signal expressing a two-dimensional image generated by converting the three-dimensional conversion target region image 250B2 into two dimensions.

In other words, the two-dimensional processed image signal is a signal expressing the two-dimensional processed image obtained by geometrically aligning the three-dimensional conversion target region image representing the three-dimensional conversion target region specified at step 308E with a corresponding position in the SLO fundus image acquired in the processing of step 300, and converting the three-dimensional conversion target region image. The two-dimensional processed image is an image formed by respective pixels of the SLO fundus image being displayed on the SLO fundus image display screen 250A, these pixels being identified from the two-dimensional position information obtained by executing the processing of above step 308G.

When the processing of step 308H is executed and the two-dimensional processed image signal is output to the display 172A by the display control section 184A, the display 172A displays the SLO fundus image in a form reflecting the two-dimensional converted image. In other words, the CPU 162 executes the processing of step 308H to control the display 172A so as to display the SLO fundus image in a form reflecting the two-dimensional converted image on the display 172A.

Namely, in a case in which a three-dimensional conversion target region has been specified in the three-dimensional image, an image, resulting from aligning the three-dimensional conversion target region image with a corresponding position in the two-dimensional image and converting the three-dimensional conversion target image, is displayed overlaid on the SLO fundus image.

In FIG. 11A (1), the outline of a two-dimensional processed image 250A2 identified by the two-dimensional position information corresponding to the three-dimensional image information relating to each of the pixels in the three-dimensional conversion target region 250B2 is displayed by single-dotted dashed lines. By displaying the outline of the two-dimensional converted image 250A2 with single-dotted dashed lines in this manner, the two-dimensional converted image 250A2 is displayed in the SLO fundus image such that the two-dimensional converted image 250A2 can be differentiated from other regions. In other words, the two-dimensional processed image 250A2 obtained by performing geometric conversion on the three-dimensional conversion target region image 250B2 is displayed in the SLO fundus image such that the two-dimensional processed image 250A2 can be differentiated from other regions.

By executing the processing of steps 308E to 308H, the three-dimensional conversion target region image is converted aligned with the geometric characteristics of the corresponding position in the SLO fundus image, and the mutually related three-dimensional conversion target region and two-dimensional processed image are displayed alongside each other on the display 172A so as to enable visual comparison therebetween.

At step 308I, the processing section 186A determines whether or not a change instruction as previously described has been received by the input/instruction device 174. The change instruction referred to at step 308I is realized by moving the display screen dividing line 252 from one side toward the other side between the SLO fundus image display screen 250A and the three-dimensional image display screen 250B.

In cases in which a change instruction has not been received by the input/instruction device 174, the determination of step 308I is negative, and the specified region observation processing transitions to step 308A. In cases in which a change instruction has been received by the input/instruction device 174, the determination of step 308I is affirmative, and the specified region observation processing transitions to step 308J.

At step 308J, the display control section 184A outputs a change instruction signal to the display 172A, and the specified region observation processing is then ended. When the change instruction signal is output to the display 172, the display 172A changes the respective display sizes of the SLO fundus image and the three-dimensional image. In other words, the CPU 162 executes the processing of step 308J so as to control the display 172A to change the respective display sizes (areas of the display regions) of the SLO fundus image and the three-dimensional image according to the change instruction received by the input/instruction device 174.

Figure 12A:
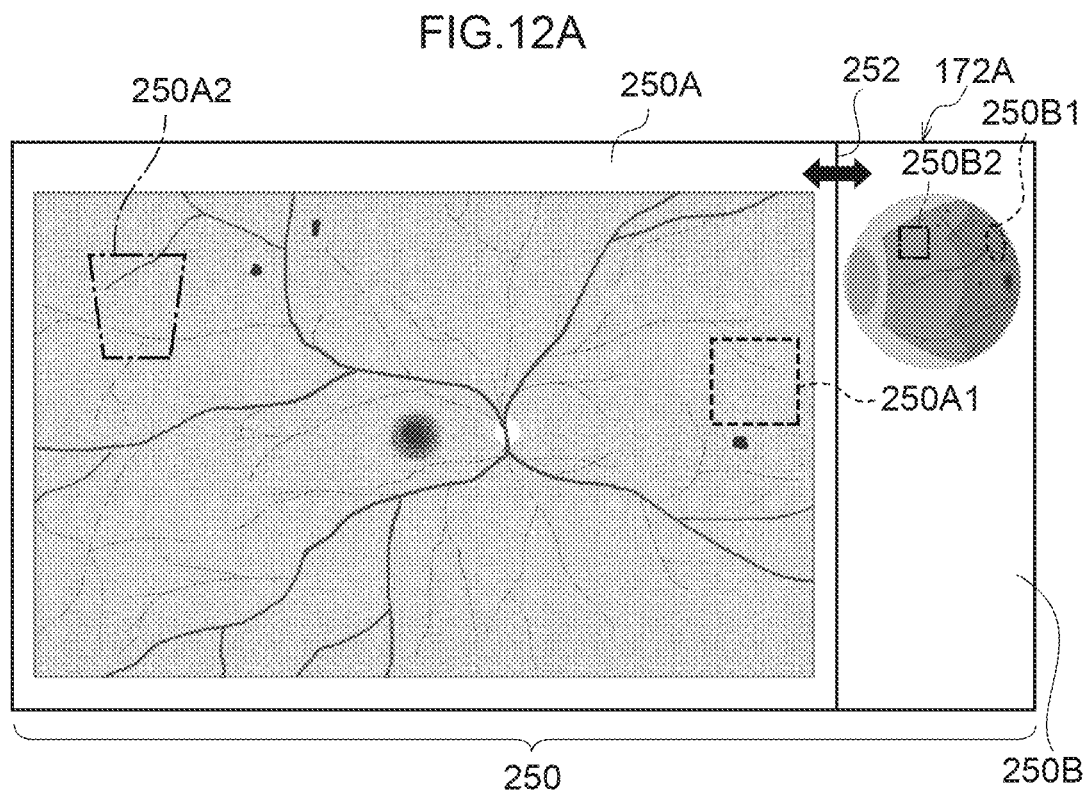
FIG. 12A is a diagram illustrating an examined eye check screen in a state displayed on a display of an image viewer, illustrating the examined eye check screen when an SLO image display screen has been magnified and a three-dimensional image display screen has been shrunk.

Specifically, as illustrated in FIG. 12A, when the display screen dividing line 252 is moved from the SLO fundus image display screen 250A side toward the three-dimensional image display screen 250B side, the display 172A magnifies the display of the SLO fundus image and shrinks the display of the three-dimensional image. In FIG. 12A, the display 172A increases the area of the SLO fundus image display screen 250A, and decreases the area of the three-dimensional image display screen 250B by an amount commensurate with the increase in the area of the SLO fundus image display screen 250A. The display 172A displays the SLO fundus image with an increased area in the SLO fundus image display screen 250A accompanying the increase in the area of the SLO fundus image display screen 250A. The display 172A also displays the three-dimensional image in the three-dimensional image display screen 250B with a decreased area accompanying the decrease in the area of the three-dimensional image display screen 250B.

In other words, the display 172A magnifies the display of the SLO fundus image by increasing the display size of the SLO fundus image display screen 250A, and shrinks the display of the three-dimensional image by reducing the display size of the three-dimensional image display screen 250B.

Figure 12B:
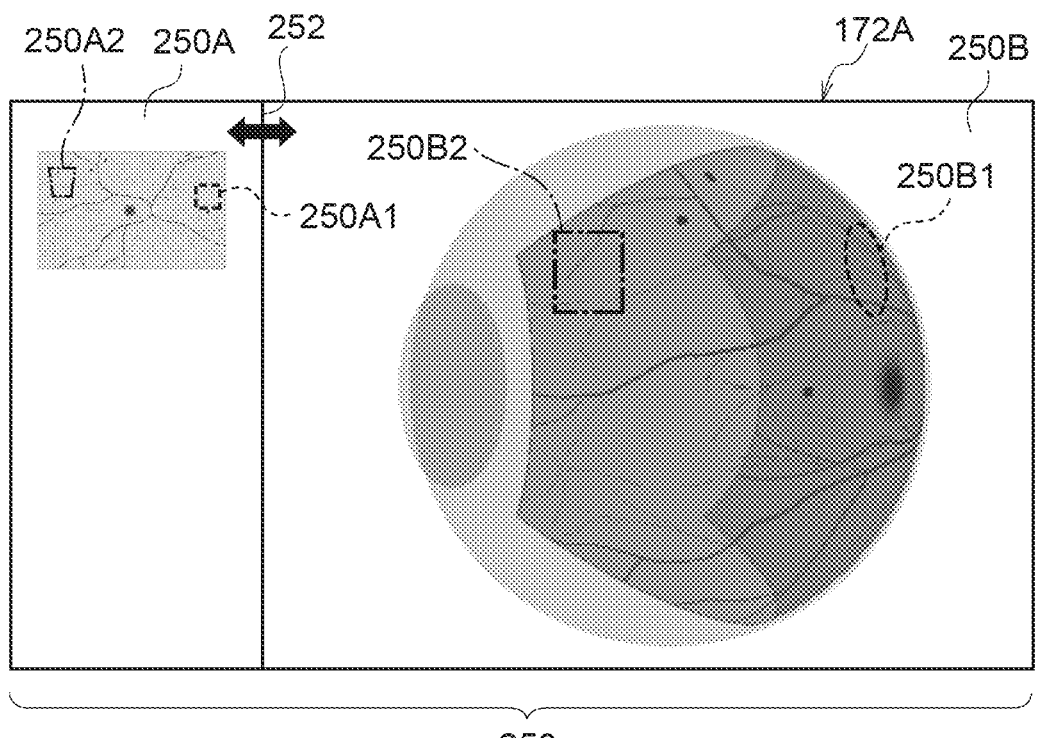
FIG. 12B is a diagram illustrating an examined eye check screen in a state displayed on a display of an image viewer, illustrating the examined eye check screen when an SLO image display screen has been shrunk and a three-dimensional image display screen has been magnified.

Moreover, as illustrated in FIG. 12B, when the display screen dividing line 252 is moved from the three-dimensional image display screen 250B side toward the SLO fundus image display screen 250A side, the display 172A magnifies the display of the three-dimensional image and shrinks the display of the SLO fundus image. In FIG. 12B, the display 172A increases the area of the three-dimensional image display screen 250B, and decreases the area of the SLO fundus image display screen 250A by an amount commensurate with the increase in the area of the three-dimensional image display screen 250B. The display 172A displays the three-dimensional image with an increased area in the three-dimensional image display screen 250B accompanying the increase in the area of the three-dimensional image display screen 250B. The display 172A also displays the SLO fundus image in the SLO fundus image display screen 250A with a decreased area accompanying the decrease in the area of the SLO fundus image display screen 250A.

In other words, the display 172A magnifies the display of the three-dimensional image by increasing the display size of the three-dimensional image display screen 250B, and shrinks the display of the SLO fundus image by reducing the display size of the SLO fundus image display screen 250A.

By executing the processing of step 308J in this manner, the CPU 162A controls the display 172A according to the change instruction received by the input/instruction device 174A of the image viewer 150 so as to change the respective display sizes of the SLO fundus image and the three-dimensional image.

At step 312 of the display control processing illustrated in FIG. 8, the processing section 186A determines whether or not an instruction received by the input/instruction device 174A is an OCT imaging assistance instruction. In cases in which the instruction received by the image input/instruction device 174A is not an OCT imaging assistance instruction, the determination of step 312 is negative, and the display control processing transitions to step 316. In cases in which the instruction received by the input/instruction device 174A is an OCT imaging assistance instruction, the determination of step 312 is affirmative, and the display control processing transitions to step 314.

At step 314, an OCT imaging position is specified by a user using the input/instruction device 174A of the image viewer 150, and the processing section 186A transmits imaging position information indicating the imaging position to the ophthalmic device 110.

At step 316, the processing section 186A determines whether or not the instruction received by the input/instruction device 174A is a laser irradiation assistance instruction. In cases in which the instruction received by the input/instruction device 174A is not a laser irradiation assistance instruction, the determination of step 316 is negative, and the display control processing transitions to step 312. In cases in which the instruction received by the input/instruction device 174A is a laser irradiation assistance instruction, the determination of step 316 is affirmative, and the display control processing transitions to step 318.

At step 318, a laser irradiation region of the laser treatment device 135 is specified by a user using the input/instruction device 174A, and the processing section 186A outputs laser irradiation position information indicating the location of the laser irradiation region to at least one out of the display 172A or the laser treatment device 135. The output destination of the laser irradiation position information is set in response to an instruction received by the input/instruction device 174A.

Figure 13:
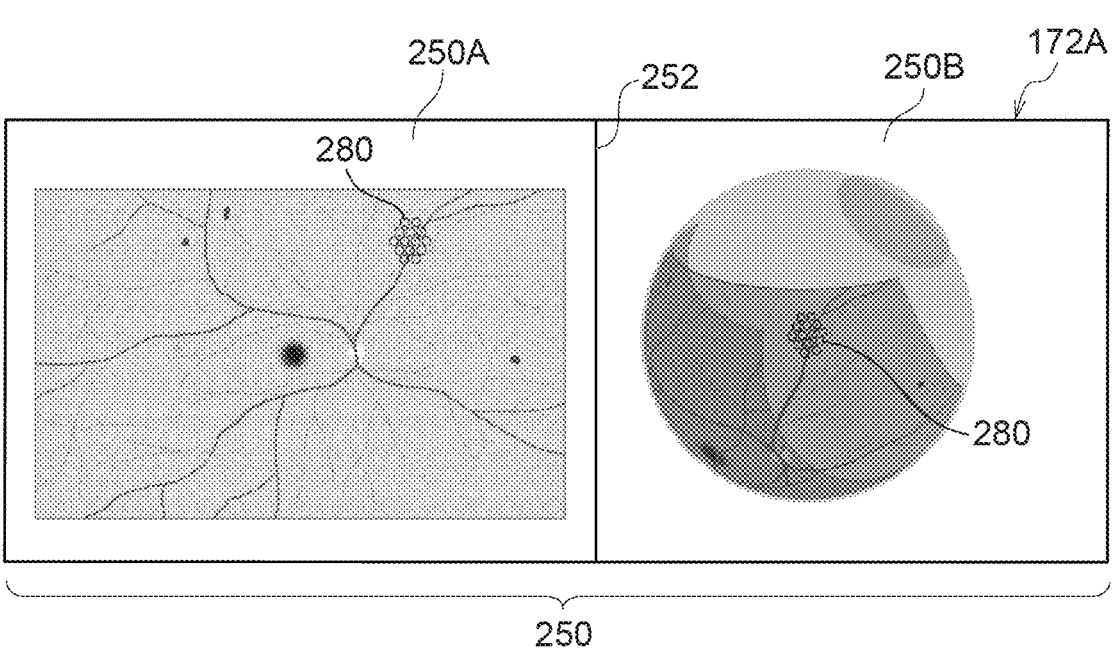
FIG. 13 is a diagram illustrating an examined eye check screen in a state displayed on a display of an image viewer.

When the laser irradiation position information is output to the display 172A, the display 172A displays laser irradiation position marks 280 as illustrated in FIG. 13. The laser irradiation position marks 280 are applied at a position corresponding to the position of the two-dimensional conversion target region image and a position corresponding to the position of the three-dimensional processed image as an indicator of a region to be irradiated with a laser by the laser treatment device 135. In FIG. 13, the laser irradiation position mark 280 in the SLO fundus image display screen 250A and the laser irradiation position mark 280 in the three-dimensional image display screen 250B are an example of "a mark indicating the second region" according to the technology disclosed herein.

In the display 172A, the laser irradiation position marks 280 are displayed overlaid at the position corresponding to the position of the two-dimensional conversion target region image and the position corresponding to the position of the three-dimensional processed image. The SLO fundus image and the three-dimensional image are displayed alongside each other on the display 172A so as to enable visual comparison of the laser irradiation position marks 280 displayed overlaid at the position corresponding to the position of the two-dimensional conversion target region image and the position corresponding to the position of the three-dimensional processed image.

Namely, by executing the processing of step 318, the CPU 162A controls the display 172A such that the SLO fundus image and the three-dimensional image are displayed in a form reflecting the laser irradiation position marks 280 at each of the position corresponding to the position of the two-dimensional conversion target region image and the position corresponding to the position of the three-dimensional processed image.

FIG. 13 displays an in-surgery two-dimensional fundus image, this being an SLO fundus image representing the examined eye 12 during laser surgery to the examined eye 12. FIG. 13 also displays an in-surgery three-dimensional image, this being a three-dimensional image representing the examined eye 12 during laser surgery to the examined eye 12. The image viewer 150 thus enables a user to ascertain the condition of the examined eye 12 during laser surgery with a high degree of precision.

However, the technology disclosed herein is not limited thereto. A post-surgery two-dimensional fundus image, this being an SLO fundus image representing the examined eye 12 after performing laser surgery on the fundus of the examined eye 12, and a post-surgery three-dimensional image, this being a three-dimensional image representing the examined eye 12 after performing laser surgery on the examined eye 12, may be displayed. In such cases, the image viewer 150 enables a user to ascertain the state of the fundus of the examined eye 12 following laser surgery with a high degree of precision.

When the laser irradiation position information is output to the laser treatment device 135, the laser treatment device 135 irradiates the position indicated by the laser irradiation position information with a laser.

Figure 16:
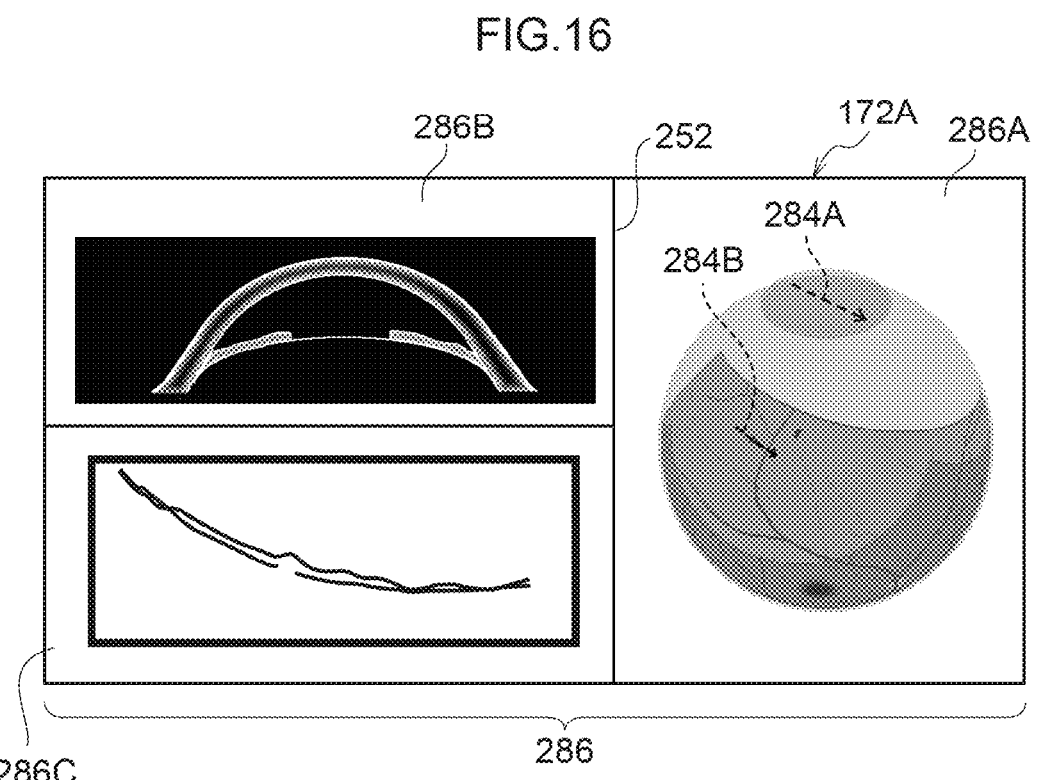
FIG. 16 is a diagram illustrating an examined eye check screen in a state displayed on a display of an image viewer.

Although explanation has been given regarding an example in which a region in an SLO fundus image or a three-dimensional image corresponding to a region of the fundus of the examined eye 12 configures a region specified by a user in the first exemplary embodiment described above, the technology disclosed herein is not limited thereto. Configuration may be made in which plural locations in a three-dimensional image are specified by a user, and OCT imaging is performed for respective locations in the examined eye 12 corresponding to each of the plural locations specified by the user. In FIG. 16, an examined eye check screen 286 is displayed on the display 172A. The examined eye check screen 286 is a screen including a three-dimensional image display screen 286A, a first OCT image display screen 286B, and a second OCT image display screen 286C. The three-dimensional image display screen 286A displays a three-dimensional image, and linear three-dimensional conversion target region 284A, 284B are displayed in the three-dimensional image at each of an anterior eye image region representing an anterior eye segment of the examined eye 12 and a posterior eye image region representing a posterior eye segment of the examined eye 12.

A two-dimensional OCT image, this being a B-scan image obtained by OCT imaging of a position corresponding to the three-dimensional conversion target region 284A in the anterior eye segment of the examined eye 12, is displayed on the first OCT image display screen 286B. A two-dimensional OCT image, this being a B-scan image obtained by OCT imaging of a position corresponding to the three-dimensional conversion target region image 284A corresponding to the retina in the posterior eye segment of the examined eye 12, is displayed on the second OCT image display screen 286C.

In FIG. 16, a two-dimensional anterior eye segment image and an SLO fundus image each corresponding to the three-dimensional image, and two-dimensional processed images corresponding to the respective three-dimensional conversion target region images 284A, 284B are not displayed. However, the technology disclosed herein is not limited thereto. A two-dimensional anterior eye segment image and an SLO fundus image each corresponding to the three-dimensional image, and two-dimensional processed images corresponding to the respective three-dimensional conversion target region images 284A, 284B may be displayed alongside the three-dimensional image and the two-dimensional OCT images on the display 172.

Display of a specified image out of a three-dimensional image including the three-dimensional conversion target region images 284A, 284B, an SLO fundus image including two-dimensional processed images, and two-dimensional OCT images corresponding to the respective three-dimensional conversion target region images 284A, 284B may be magnified.

As described above, in the first exemplary embodiment, a SLO fundus image and a three-dimensional image are acquired by the image processing section 182A. In cases in which a two-dimensional conversion target region has been specified in a state in which the SLO fundus image out of the acquired SLO fundus image and three-dimensional image is being displayed on the display 172A, a three-dimensional processed image, resulting from aligning the two-dimensional conversion target region image with a corresponding position in the three-dimensional image out of the acquired SLO fundus image and three-dimensional image and converting the two-dimensional conversion target region image, is displayed overlaid on the three-dimensional image. The image viewer 150 thus enables a user to ascertain a region of interest in the examined eye with a high degree of precision.

In the first exemplary embodiment, in cases in which a three-dimensional conversion target region has been specified in a state in which the three-dimensional image out of the SLO fundus image and three-dimensional image acquired by the image processing section 182A is being displayed on the display 172A, a two-dimensional processed image, resulting from aligning the three-dimensional conversion target region image with a corresponding position in the SLO fundus image and converting the three-dimensional conversion target region image, is displayed overlaid on the SLO fundus image. The image viewer 150 thus enables a user to ascertain a region of interest in the examined eye with a high degree of precision.

In the first exemplary embodiment, the display control section 184A displays the SLO fundus image overlaid with the two-dimensional processed image on the display 172A. The image viewer 150 thus enables a user to easily ascertain the position of the two-dimensional processed image in the SLO fundus image.

In the first exemplary embodiment, the display control section 184A displays the three-dimensional image overlaid with the three-dimensional processed image on the display 172A. The image viewer 150 thus enables a user to easily ascertain the position of the three-dimensional processed image in the three-dimensional image.

In the first exemplary embodiment, in cases in which the first pre-set condition or the second pre-set condition described previously has been satisfied, the display control section 184A outputs a rotate-and-display instruction signal instructing rotation and display to the display 172A, such that the three-dimensional image is rotated and displayed and the three-dimensional processed image is displayed at a position where it can be seen. The image viewer 150 thus enables a user to easily ascertain the entirety of a specified region in the examined eye irrespective of the size and position of the three-dimensional processed image in the three-dimensional image.

In the first exemplary embodiment, the display control section 184A displays the two-dimensional image and the three-dimensional image alongside each other on the display 172A so as to enable visual comparison therebetween. The image viewer 150 thus enables a user to ascertain a region of interest (in particular the fundus) in the examined eye with a high degree of precision.

In the first exemplary embodiment, in cases in which a change instruction has been given, the display control section 184A outputs a change instruction signal to the display 172A so as to change the respective display sizes of the two-dimensional image and the three-dimensional image on the display 172A. The image viewer 150 thus enables the two-dimensional image and the three-dimensional image to be displayed on the display 172A at display sizes requested by a user.

In the first exemplary embodiment, the display control section 184A displays the two-dimensional image, the three-dimensional image, and the OCT image alongside each other on the display 172A so as to enable visual comparison therebetween. The image viewer 150 thus enables a user to ascertain a region of interest in the examined eye with a high degree of precision.

In the first exemplary embodiment, in cases in which a magnified display instruction has been given, the display control section 184A outputs a magnified display instruction signal to the display 172A so as to magnify display of the OCT image on the display 172A. The image viewer 150 thus enables a user to easily ascertain the entirety of a specified region in the examined eye using the OCT image.

In the first exemplary embodiment, in cases in which a conversion target region has a linear shape, a two-dimensional OCT image is displayed on the display 172A, and in cases in which a conversion target region has a planar shape, a three-dimensional OCT image is displayed on the display 172A. The image viewer 150 is thus capable of selectively presenting a user with a two-dimensional OCT image or a three-dimensional OCT image by a simple operation.

In the first exemplary embodiment, the display control section 184A outputs a two-dimensional processed image signal to the display 172A so as to display a SLO fundus image on the display 172A in a form reflecting a laser illumination position mark at a position corresponding to the position of the two-dimensional processed image. The image viewer 150 thus enables a user to ascertain the position to be irradiated by a surgical laser with a high degree of precision.

In the first exemplary embodiment, the display control section 184A outputs a three-dimensional processed image signal to the display 172A so as to display a three-dimensional image on the display 172A in a form reflecting a laser illumination position mark at a position corresponding to the position of the three-dimensional processed image. The image viewer 150 thus enables a user to ascertain the position to be irradiated by a surgical laser with a high degree of precision.

In the first exemplary embodiment, a vascular area or an avascular area is detected by the image processing section 182A from the SLO fundus image and/or the three-dimensional image, and the vascular area is specified as a conversion target region based on the detection results of the image processing section 182A. The image viewer 150 thus enables a user to ascertain the position of a lesion with a high degree of precision.

In the first exemplary embodiment, a neovascular area is detected by the image processing section 182A, and the detected neovascular area is specified as a conversion target region. The image viewer 150 thus enables a user to ascertain the position of a lesion with a high degree of precision.

In the first exemplary embodiment, in cases in which each of plural locations in a first image have been specified as conversion target regions, processed images are generated for each of the specified conversion target regions. The image viewer 150 thus enables a user to ascertain the positions of plural regions of interest with a high degree of precision.

In the first exemplary embodiment, in cases in which each of plural locations including an anterior eye segment and a posterior eye segment of the examined eye 12 have been specified as conversion target regions, processed images are generated for each of the specified conversion target regions. The image viewer 150 thus enables a user to ascertain the positions of respective regions of interest in each of the anterior eye segment and the posterior eye segment of the examined eye 12 with a high degree of precision.

Note that in the first exemplary embodiment, in the case of a linear conversion target region, a member of staff operating the ophthalmic device 110 sets the ophthalmic device 110 to perform OCT imaging in order to generate a two-dimensional OCT image while referring to the linear conversion target region in the SLO fundus image and the linear converted image in the three-dimensional image. In the case of a planar conversion target region, the ophthalmic device 110 is set so as to perform OCT imaging in order to obtain a three-dimensional OCT image while referring to the planar conversion target region in the SLO fundus image and the planar converted image in the three-dimensional image.

However, the technology disclosed herein is not limited thereto. Configuration may be made such that the CPU 16A controls the OCT unit 20 and the image capture optical system 19 such that signal light is scanned during OCT imaging according to (yX, (pY) associated with each of the pixels in the conversion target region or converted image described above so as to obtain a two-dimensional or three-dimensional OCT image. In such cases, the effort required of the member of staff in order to obtain a two-dimensional OCT image or a three-dimensional OCT image can be reduced. Namely, the ophthalmic device 110 executes OCT imaging of a location corresponding to the specified conversion target region as long as the ophthalmologist has specified a conversion target region using the image viewer 150 in the examination room. The ophthalmologist is thus able to obtain an OCT image obtained by OCT imaging for their requested location in the fundus of the examined eye 12. Namely the ophthalmologist is able to obtain a two-dimensional OCT image if they have specified a linear conversion target region, and is able to obtain a three-dimensional OCT image if they have specified a planar conversion target region using the image viewer 150 in the examination room.

In each of the exemplary embodiment described above, explanation has been given regarding an example in which, in cases in which a two-dimensional conversion target region has been specified in the SLO fundus image, an image, resulting from aligning the two-dimensional conversion target region with a corresponding position in the three-dimensional image and converting a two-dimensional conversion target image, is displayed overlaid on the three-dimensional image (step 308A to step 308D in FIG. 10). However, the technology disclosed herein is not limited thereto. A three-dimensional image may be generated by converting the SLO fundus image overlaid with the two-dimensional conversion target region into three dimensions, and the generated three-dimensional image may be displayed. Such cases enable similar advantageous effects to those of the exemplary embodiment described above.

In the first exemplary embodiment, explanation has been given regarding an example in which, in cases in which a three-dimensional conversion target region has been specified in the three-dimensional image, an image, resulting from aligning the three-dimensional conversion target region with a corresponding position in the SLO fundus image and converting the three-dimensional conversion target image, is displayed overlaid on the two-dimensional image (step 308E to step 308H illustrated in FIG. 10). However, the technology disclosed herein is not limited thereto. For example, a two-dimensional image may be generated by converting the three-dimensional image overlaid with the three-dimensional conversion target region into two dimensions, and the generated two-dimensional image may be displayed. Such cases enable similar advantageous effects to those of the exemplary embodiment described above.

In the first exemplary embodiment, explanation has been given regarding an example in which the display control processing is executed by the image viewer 150. However, the technology disclosed herein is not limited thereto. The display control processing may be executed by the ophthalmic device 110 or by the management server 140, or may be executed by at least one out of the ophthalmic device 110, the management server 140, the image viewer 150, or another device. The display control processing may be also executed with the processing distributed between two or more out of the ophthalmic device 110, the management server 140, the image viewer 150, or another device.

In the first exemplary embodiment, explanation has been given regarding an example in which the control program is read from the memory 164. However, the control program does not necessarily have to be stored in the memory 164 from the outset. The control program may initially be stored on a non-transient computer-readable portable storage medium such as a solid state drive (SSD), universal serial bus (USB) memory, or digital versatile disc read only memory (DVD-ROM). In such cases, relevant programs on the storage medium are installed to the image viewer 150 and the installed control program is then executed by the CPU 162. Note that although an example of a portable storage medium has been given, an inbuilt storage medium may be employed.

Alternatively, the control program may be stored in a storage section of for example another computer or server device coupled to the image viewer 150 over a communication network (not illustrated in the drawings), and the control program may be downloaded and installed in response to a request from the image viewer 150. In such cases, the installed control program is executed by the CPU 162.

The display control processing as explained in the first exemplary embodiment is merely an example thereof. Obviously, unnecessary steps may be omitted, new steps may be added, or the processing sequence may be rearranged within a range not departing from the spirit of the present disclosure.

Although explanation has been given in the first exemplary embodiment regarding an example in which a computer is employed to implement display control processing using a software configuration, the technology disclosed herein is not limited thereto. For example, instead of a software configuration employing a computer, the display control processing may be executed solely by a hardware configuration such as a field-programmable gate array (FPGA) or an application specific integrated circuit (ASIC). Alternatively, a configuration may be adopted in which the display control processing is executed by a combination of software configurations and hardware configurations.

Examples of hardware resources used to execute the various processing of the display control processing and so on include a CPU configured by a generic processor that functions as a hardware resource to execute the various processing by executing a program. Other examples of hardware resources include dedicated electrical circuits configured by processors provided with circuit configurations such as a tailor-made FPGA, programmable logic device (PLD), or ASIC. The hardware structures of such processors may employ electrical circuits including a combination of circuit elements such as semiconductor elements. The hardware resources used to execute the various processing may employ a single type of processor out of the plural types of processor described above, or may employ a combination of two or more processors of the same type or of different types to each other.

Second Exemplary Embodiment

In a second exemplary embodiment, configuration elements equivalent to configuration elements explained the first exemplary embodiment are allocated the same reference numerals, and explanation thereof is omitted.

The memory 164 is stored with a 2D/3D display screen generation program. The CPU 162 reads the 2D/3D display screen generation program from the memory 164 and executes the read 2D/3D display screen generation program.

The memory 164 is also stored with an OCT display screen generation program. The CPU 162 reads the OCT display screen generation program from the memory 164 and executes the read OCT display screen generation program.

Figure 17:
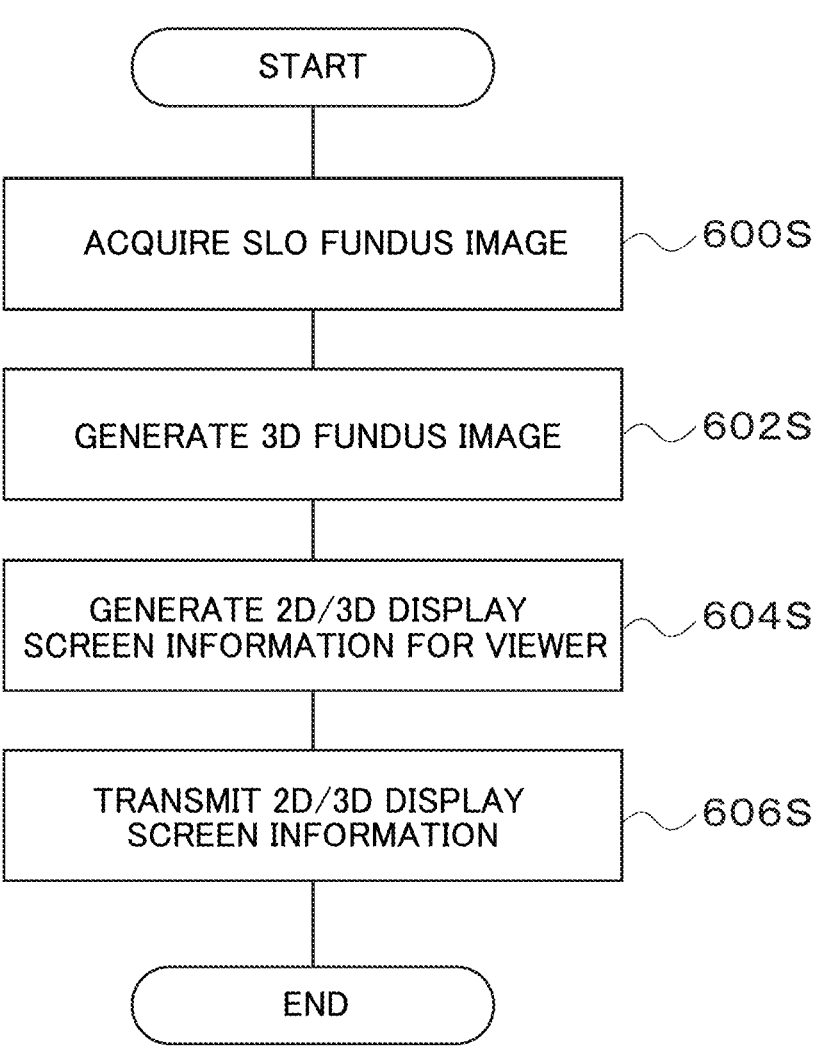
FIG. 17 is a flowchart illustrating a flow of 2D/3D display screen generation processing.

FIG. 17 illustrates a flow of 2D/3D display screen generation processing realized by the CPU 162 executing the 2D/3D display screen generation program.

In the 2D/3D display screen generation processing illustrated in FIG. 17, at step 600S, the image processing section 182 acquires a UWF-SLO fundus image obtained by imaging the fundus of the examined eye with the ophthalmic device 110 from the ophthalmic device 110.

At the next step 602S, the image processing section 182 generates a 3D fundus image by performing image conversion on the UWF-SLO fundus image acquired from the ophthalmic device 110. The 3D fundus image is a three-dimensional image representing the fundus. The image processing section 182 generates the 3D fundus image utilizing the method used to convert a two-dimensional image into a three-dimensional image described in the first exemplary embodiment.

At the next step 604S, the image processing section 182 generates 2D/3D display screen information expressing a 2D/3D display screen 600, illustrated in FIG. 18, for the viewer.

At the next step 606S, the image processing section 182 transmits the 2D/3D display screen information to the image viewer 150, after which the 2D/3D display screen generation processing is ended.

When the 2D/3D display screen information is transmitted to the image viewer 150 by executing the processing of step 606S of the 2D/3D display screen generation processing, the display control section 184 receives the 2D/3D display screen information. As illustrated in FIG. 18, the display control section 184 displays the 2D/3D display screen 600 expressed by the received 2D/3D display screen information on the display 172.

Note that in FIG. 18, the UWF-SLO fundus image 400S1, this being an example of an SLO fundus image acquired by executing the processing of step 600S, and the three-dimensional image 400S2, this being a 3D fundus image generated by executing the processing of step 602S, are displayed alongside each other in the examined eye check screen 250.

Figure 19A:
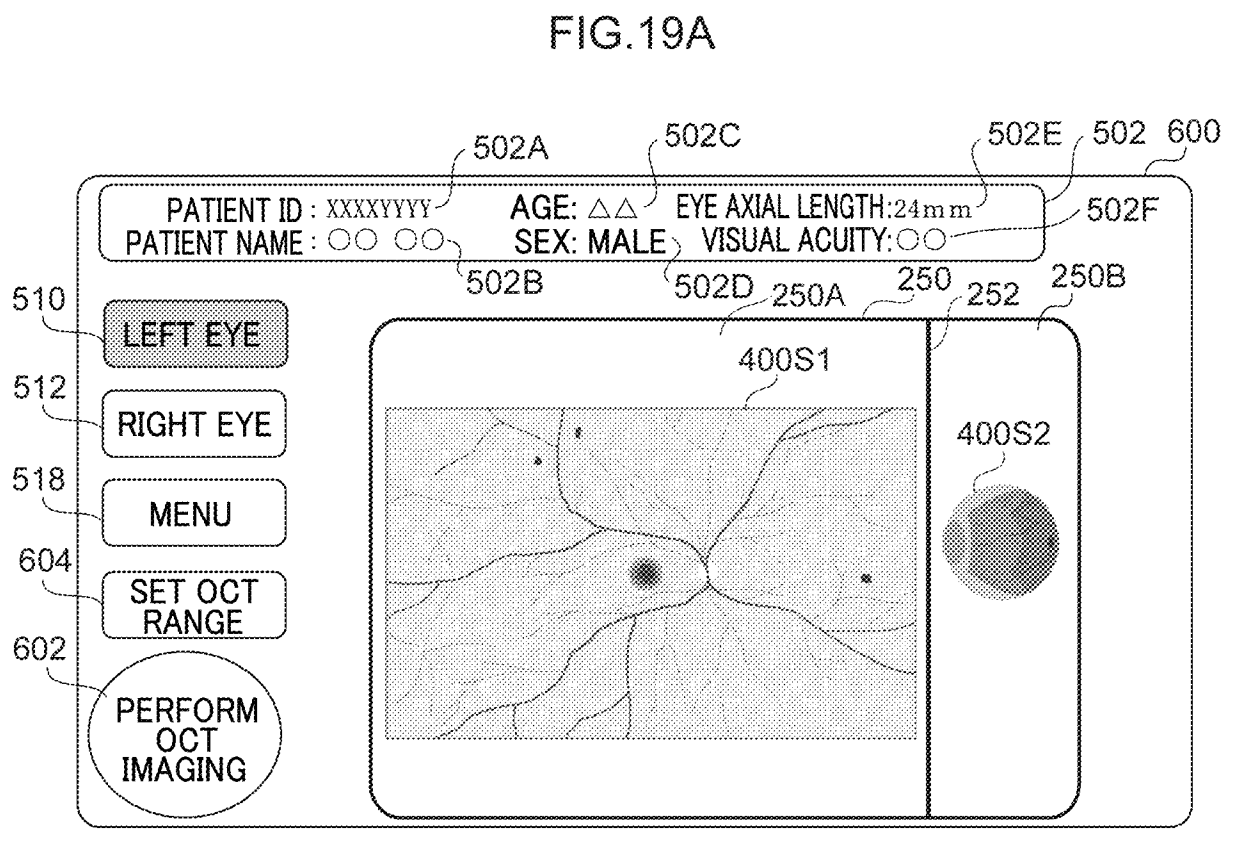

In FIG. 19A, similarly to in FIG. 12A, when the display screen dividing line 252 is moved from the SLO fundus image display screen 250A side toward the three-dimensional image display screen 250B side, the display 172 magnifies display of the UWF-SLO fundus image 400S1 and shrinks display of the three-dimensional image 400S2 under the control of the display control section 184.

Moreover, in FIG. 19B, similarly to in FIG. 12B, when the display screen dividing line 252 is moved from the three-dimensional image display screen 250B side toward the SLO fundus image display screen 250A side, the display 172 magnifies display of the three-dimensional image 400S2 and shrinks display of the UWF-SLO fundus image 400S1 under the control of the display control section 184.

Figure 20:
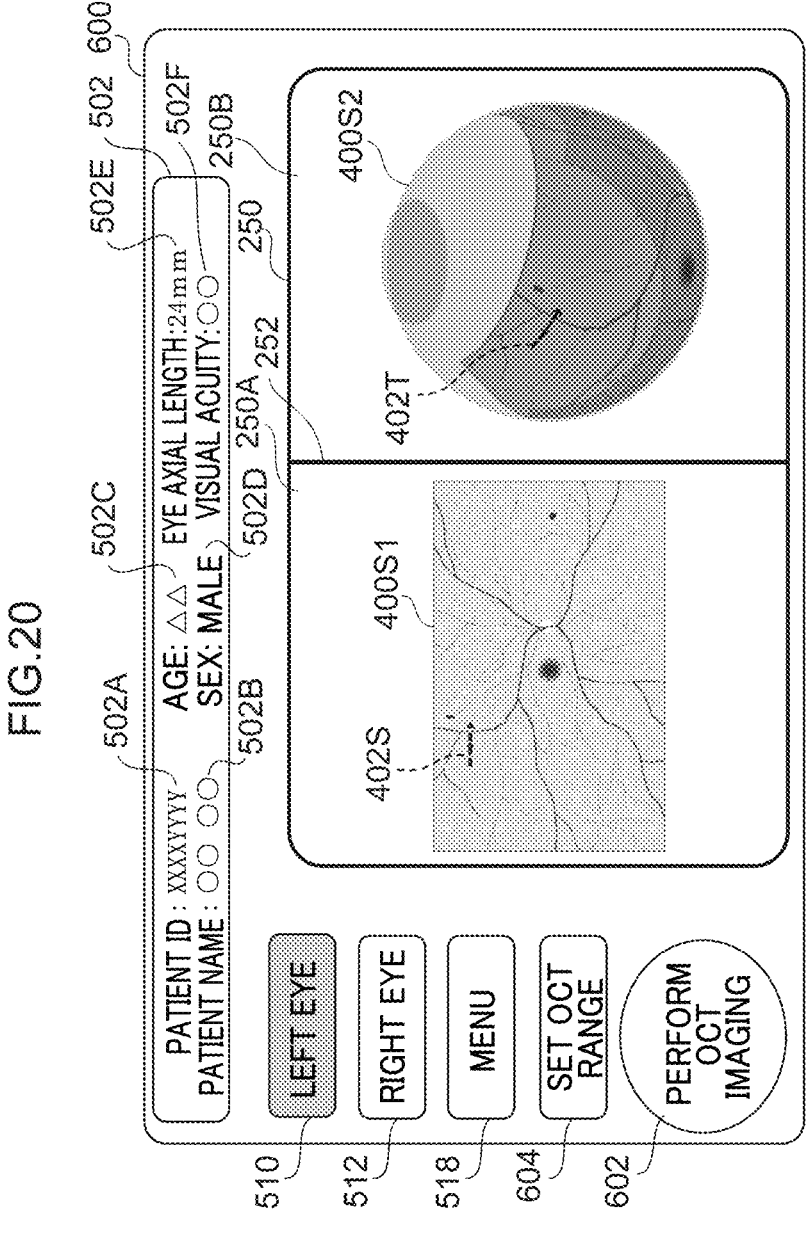
FIG. 20 is a diagram illustrating a 2D/3D display screen.

As illustrated in FIG. 20, the image processing section 182 creates a line segment arrow 402S indicating an OCT acquisition position in the UWF-SLO fundus image 400S1.

The line segment arrow 402S is a mark corresponding to the two-dimensional conversion target region 250A3 illustrated in FIG. 14A. The position, shape, and size of the line segment arrow 402S are set in response to instructions received through the input/instruction device 174 or the input/instruction device 174A. Namely, a user uses the input/instruction device 174 or the input/instruction device 174A to specify the position, shape, and size of the line segment arrow 402S in the UWF-SLO fundus image 400S1. Note that the position of the line segment arrow 402S is an example of a "first psotion specified in the two-dimensional fundus image" according to the technology disclosed herein.

When the line segment arrow 402S has been set, the image processing section 182 finds the position on the 3D image. The position on the 3D image is an example of "a second region in the three-dimensional eyeball image" according to the technology disclosed herein. The position on the 3D image is a position on the 3D image corresponding to the specified position of the line segment arrow 402S in the UWF-SLO fundus image 400S1. The position on the 3D image is, for example, found by the image processing section 182 executing similar processing to the processing of step 308A to step 308D of the specified region observation processing illustrated in FIG. 10.

When the position on the 3D image has been found, the image processing section 182 creates a circular arched arrow 402T based on the position on the 3D image as illustrated in FIG. 20. The image processing section 182 then creates the three-dimensional image 400S2 with the circular arched arrow 402T overlaid thereon.

The management server 140 then controls the ophthalmic device 110 such that the ophthalmic device 110 performs optical coherence tomography imaging, namely OCT imaging by the OCT unit 20, on a region in the examined eye identified by the region of the line segment arrow 402S and the region of the circular arched arrow 402T.

In this manner, in the second exemplary embodiment the position of the line segment arrow 402S and the position of the circular arched arrow 402T configure the position where optical coherence tomography imaging, namely OCT imaging by the OCT unit 20, is to be performed. Note that the circular arched arrow 402T is an example of a "mark indicating the second region" according to the technology disclosed herein.

The image processing section 182 acquires an OCT image obtained by performing OCT imaging, and stores the OCT image in the memory 164. The OCT image referred to here is an OCT image created based on OCT data acquired by the OCT unit 20.

Figure 21:
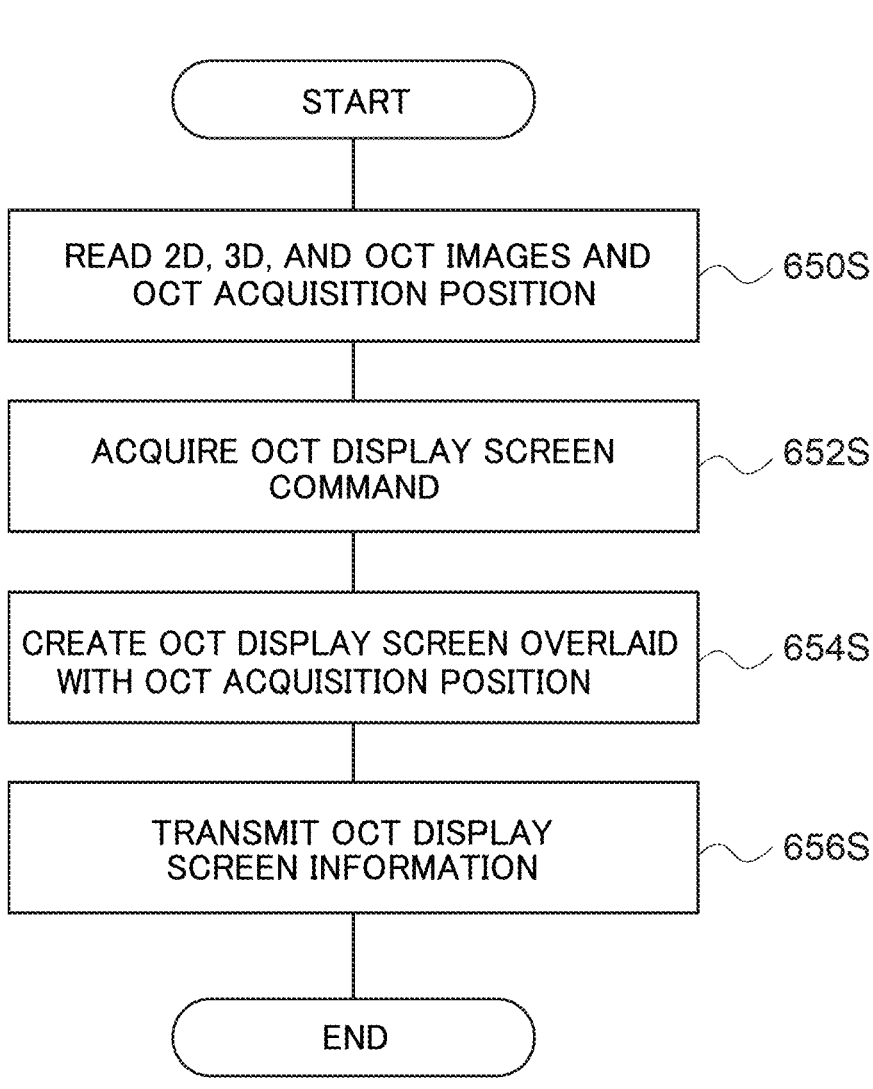
FIG. 21 is a flowchart illustrating a flow of OCT display screen generation processing.

FIG. 21 illustrates a flow of OCT display screen generation processing realized by the CPU 162 executing the OCT display screen generation program. Note that for the sake of convenience, explanation regarding the flowchart illustrated in FIG. 21 assumes that a 2D image, a 3D image, and an OCT image have already been stored in the memory 164. The 2D image referred to here is a UWF-SLO fundus image acquired by executing the processing of step 600S of the 2D/3D display screen generation processing illustrated in FIG. 17. The 3D image referred to here is a 3D fundus image generated by executing the processing of step 602S of the 2D/3D display screen generation processing illustrated in FIG. 17.

In the OCT display screen generation processing illustrated in FIG. 21, first, at step 650S, the image processing section 182 reads the 2D image, the 3D image, the OCT image, and the OCT acquisition position from the memory

164. The OCT acquisition position is the position of the line segment arrow 402S in the UWF-SLO fundus image 400S1.

At the next step 652S, the image processing section 182 acquires an OCT display screen command. The OCT display screen command is a command to start display of an OCT display screen 700 illustrated in FIG. 22 on the display 172. The OCT display screen command is given by a user using a reception device (not illustrated in the drawings). The input/instruction device 174 is an example of a reception device. Other examples of reception devices include a keyboard, mouse, and/or a touch panel or the like coupled to an external device that is capable of communicating with the management server 140. The ophthalmic device 110, the image viewer 150, and the like are examples of external devices that are capable of communicating with the management server 140.

At the next step 654S, the image processing section 182 creates an OCT display screen overlaid with the OCT acquisition position.

Figure 22:
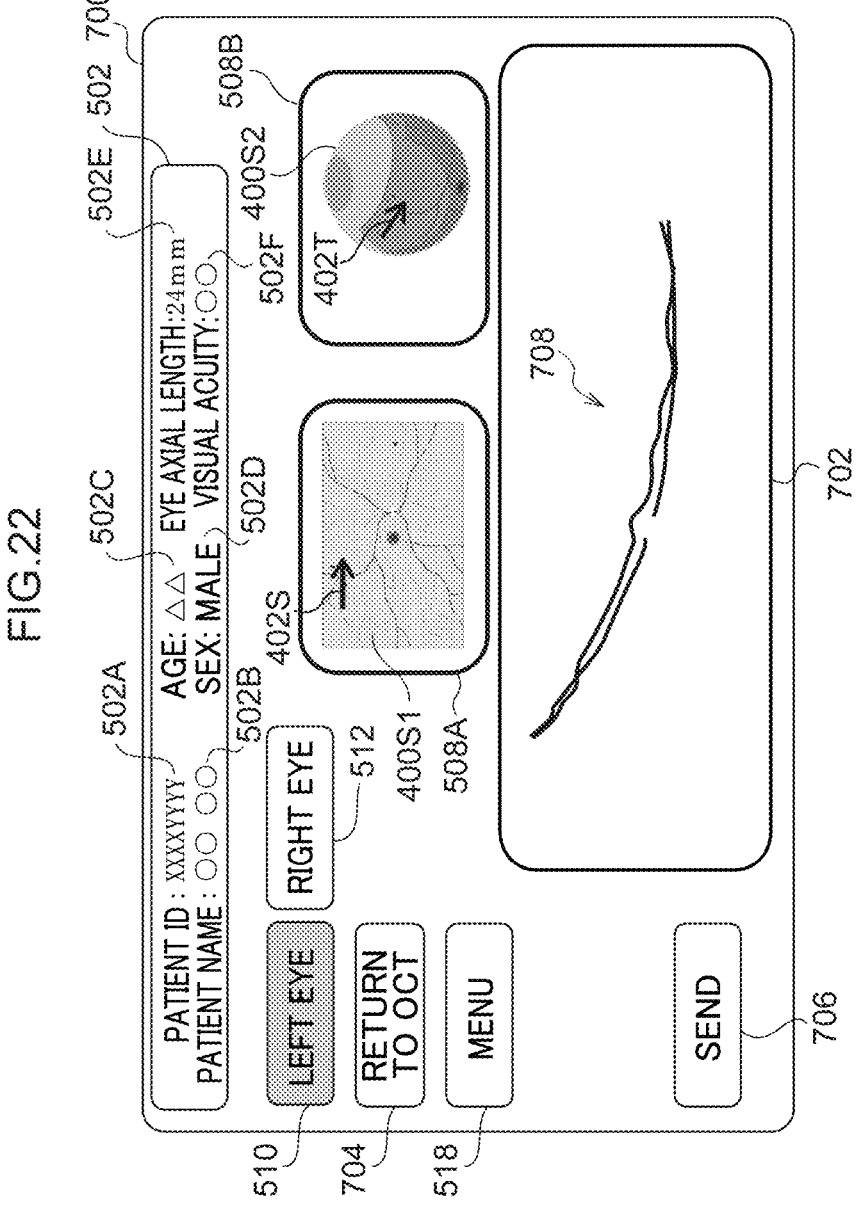
FIG. 22 is a diagram illustrating an OCT display screen.

At step 654S, as illustrated in FIG. 22, the OCT display screen 700 including the UWF-SLO fundus image 400S1 with the line segment arrow 402S overlaid thereon, the three-dimensional image 400S2 with the circular arched arrow 402T overlaid thereon, and the OCT image read by executing the processing of step 650S is created by the image processing section 182.

At the next step 656S, the display control section 184 transmits the OCT display screen information expressing the OCT display screen 700 created in the processing of step 654S to the image viewer 150, after which the OCT display screen generation processing is ended.

When the OCT display screen information is transmitted to the image viewer 150 by executing the processing of step 656S of the OCT display screen generation processing, the display control section 184 receives the OCT display screen information. As illustrated in FIG. 22, the display control section 184 displays the OCT display screen 700 expressed by the received OCT display screen information on the display 172.

As illustrated in FIG. 22, the OCT display screen 700 differs from the 2D/3D display screen 600 illustrated in FIG. 18 in the inclusion of an SLO fundus image display screen 508A instead of the SLO fundus image display screen 250A and in the inclusion of a three-dimensional image display screen 508B instead of the three-dimensional image display screen 250B. The OCT display screen 700 also differs from the 2D/3D display screen 600 illustrated in FIG. 18 in the inclusion of a tomographic image display screen 702.

The UWF-SLO fundus image 400S1 overlaid with the line segment arrow 402S is displayed on the SLO fundus image display screen 508A. The three-dimensional image 400S2 overlaid with the circular arched arrow 402T is displayed on the three-dimensional image display screen 508B. An OCT image 708 obtained by OCT imaging of a region of the examined eye identified by the position of the line segment arrow 402S and the position of the circular arched arrow 402T is displayed in the tomographic image display screen 702.

Although explanation has been given regarding an example in which the line segment arrow 402S is converted into the circular arched arrow 402T in the OCT display screen generation processing illustrated in FIG. 21, the technology disclosed herein is not limited thereto. Configuration may be made such that the position, shape, and size of the circular arched arrow 402T on the 3D image are first specified by a user, and the specified circular arched arrow 402T is then converted into the line segment arrow 402S.

This means that a position on the UWF-SLO fundus image 400S1 corresponding to the specified position of the circular arched arrow 402T on the 3D image is found by the image processing section 182.

Conversion of the circular arched arrow 402T to the line segment arrow 402S is realized by the image processing section 182 executing processing similar to the processing of step 308E to step 308H of the specified region observation processing illustrated in FIG. 10. Note that when converting the circular arched arrow 402T to the line segment arrow 402S, the region of the circular arched arrow 402T is an example of a "first region specified on the three-dimensional eyeball image" according to the technology disclosed herein, and the region of the line segment arrow 402S is an example of a "second region on the two-dimensional fundus image" according to the technology disclosed herein. Moreover, when converting the circular arched arrow 402T to the line segment arrow 402S, the line segment arrow 402S is an example of a "mark indicating the second region" according to the technology disclosed herein.

A region of the examined eye identified from the position of the line segment arrow 402S and the position of the circular arched arrow 402T may be subjected to laser treatment by the laser treatment device 135. Namely, the position of the line segment arrow 402S and the position of the circular arched arrow 402T may be employed as the position to perform laser treatment.

Although a case in which the 2D/3D display screen generation processing is executed by the management server 140 has been explained in the above second exemplary embodiment, the technology disclosed herein is not limited thereto. The 2D/3D display screen generation processing may be executed by the ophthalmic device 110, the laser treatment device 135, or the image viewer 150. The 2D/3D display screen generation processing may also be executed with the processing distributed between two or more devices out of the ophthalmic device 110, the laser treatment device 135, the management server 140, or the image viewer 150.

Although explanation has been given regarding a case in which the OCT display screen generation processing is executed by the management server 140 in the above second exemplary embodiment, the technology disclosed herein is not limited thereto. The OCT display screen generation processing may be executed by the ophthalmic device 110, the laser treatment device 135, or the image viewer 150. The OCT display screen generation processing may also be executed with the processing distributed between two or more devices out of the ophthalmic device 110, the laser treatment device 135, the management server 140, or the image viewer 150.

Although explanation has been given regarding a case in which a two-dimensional image (2D image) is configured by the UWF-SLO fundus image obtained by imaging the fundus of the examined eye in the above second exemplary embodiment, an anterior eye segment image of the anterior eye segment of the examined eye may configure the two-dimensional image. In such cases, the three-dimensional image (3D image) may employ a three-dimensional eyeball image configured by the anterior eye segment and a posterior eye segment generated from an eyeball model.

Although explanation has been given regarding an example of a case in which the 2D/3D display screen generation program and the OCT display screen generation program (referred to hereafter as the "screen generation programs") are read from the memory 164 in the above second exemplary embodiment, the screen generation programs do not necessarily have to be stored in the memory

164 from the outset. The control programs may initially be stored on a desired portable storage medium such as a SSD, USB memory, or a DVD-ROM. In such cases, the screen generation programs on the storage medium are installed in the ophthalmic device 110, the management server 140, the image viewer 150, or the like, and the installed screen generation programs are then executed by a CPU.

Alternatively, the screen generation programs may be stored in a storage section of a another computer, server device, or the like coupled to the ophthalmic device 110, the management server 140, or the image viewer 150 over a communication network (not illustrated in the drawings), and the screen generation programs may be downloaded and then installed in response to a request from the ophthalmic device 110, the management server 140, or the image viewer 150. In such cases, the installed screen generation programs are executed by a CPU.

The 2D/3D display screen generation processing and the OCT display screen generation processing as explained in the above second exemplary embodiment are merely examples thereof. Obviously, unnecessary steps may be omitted, new steps may be added, or the processing sequence may be rearranged within a range not departing from the spirit of the technology disclosed herein.

Although explanation has been given in the above second exemplary embodiment regarding an example in which a computer is employed to implement the 2D/3D display screen generation processing and the OCT display screen generation processing using a software configuration, the technology disclosed herein is not limited thereto. For example, instead of a software configuration employing a computer, at least one type of processing out of the 2D/3D display screen generation processing and the OCT display screen generation processing may be executed solely by a hardware configuration such as an FPGA or an ASIC. Alternatively, a configuration may be adopted in which at least one type of processing out of the 2D/3D display screen generation processing and the OCT display screen generation processing is executed by a combination of software configurations and hardware configurations.

Examples of hardware resources used to execute the various processing of the 2D/3D display screen generation processing and the OCT display screen generation processing include a CPU configured by a generic processor that functions as a hardware resource to execute the various processing by executing a program. Other examples of hardware resources include dedicated electrical circuits configured by processors provided with circuit configurations such as a tailor-made FPGA, PLD, or ASIC. The hardware structures of such processors may employ electrical circuits including a combination of circuit elements such as semiconductor elements. The hardware resources used to execute the various processing may employ a single type of processor out of the plural types of processor described above, or may employ a combination of two or more processors of the same type or of different types to each other.

The technology disclosed herein is capable of displaying to a user a position on a three-dimensional image corresponding to a specified region on a two-dimensional image, or a position on a two-dimensional image corresponding to a specified region on a three-dimensional image, in a manner that is easy to understand.

The technology disclosed herein is also capable of displaying to a user not only a position on a region, but also a shape on a three-dimensional image corresponding to the shape of a specified region on a two-dimensional image, or a shape on a two-dimensional image corresponding to the shape of a specified region on a three-dimensional image.

In particular, in cases in which OCT data relating to the vicinity of the fundus, an equatorial portion of the eyeball, or the like is acquired, the user is able to check the position from which the OCT data was acquired in both a two-dimensional image and a three-dimensional image. In cases in which OCT data relating to a lesion such as a detached retina positioned in the vicinity of the fundus is acquired, cases in which OCT data relating to the position of a vortex vein positioned in the vicinity of the fundus is acquired, and the like, positions from which to acquire OCT data can be specified while checking the lesion position and the positions of structures in the fundus in a two-dimensional image or a three-dimensional image.

The content of the explanation and drawings described above are detailed explanations of elements pertaining to the technology disclosed herein, and are merely examples of the technology disclosed herein. For example, explanation regarding the configurations, functions, operation, and advantageous effects described above is explanation regarding examples of the configurations, functions, operation, and advantageous effects of the technology disclosed herein. Obviously, unnecessary elements may be deleted, and new elements may be added or substituted with respect to the content of the explanation and drawings described above within a range not departing from the spirit of the technology disclosed herein. In order to avoid confusion and facilitate understanding of elements pertaining to the technology disclosed herein, the content of the explanation and drawings described above omits explanation of technical points that are common knowledge and do not require specific explanation in order to implement the technology disclosed herein.

In this specification, the term "A and/or B" is synonymous with "at least one out of A or B". Namely, "A and/or B" may signify A alone, B alone, or a combination of both A and B. In this specification, in cases in which three or more elements are grouped using "and/or" phrasing, a similar concept to that for "A and/or B" applies.

All cited documents, patent applications, and technical standards mentioned in the present specification are incorporated by reference in the present specification to the same extent as if each individual cited document, patent application, or technical standard was specifically and individually indicated to be incorporated by reference.

Supplements

The following supplements are proposed based on the content described above.

Supplement 1

An ophthalmic device including a display section, a processor, and an OCT unit, wherein the processor is configured to:

display a screen including a two-dimensional fundus image of an examined eye and a three-dimensional eyeball image of the examined eye on the display section;

find a second region in the three-dimensional eyeball image that corresponds to a first region specified in the two-dimensional fundus image;

display a mark indicating the second region in the three-dimensional eyeball image on the display section; and control the OCT unit based on the first region.

Supplement 2

An ophthalmic device including a display section, a processor, and an OCT unit, wherein the processor is configured to:

display a screen including a two-dimensional fundus image of an examined eye and a three-dimensional eyeball image of the examined eye on the display section;

find a second region in the two-dimensional fundus image that corresponds to a first region specified in the three-dimensional eyeball image;

display a mark indicating the second region in the two-dimensional fundus image on the display section; and control the OCT unit based on the first region.

Supplement 3

A laser treatment device including a display section, a processor, and a laser treatment unit, wherein the processor is configured to:

display a screen including a two-dimensional fundus image of an examined eye and a three-dimensional eyeball image of the examined eye on the display section;

find a second region in the three-dimensional eyeball image that corresponds to a first region specified in the two-dimensional fundus image;

display a mark indicating the second region in the three-dimensional eyeball image on the display section; and control the laser treatment unit based on the first region.

Supplement 4

A laser treatment device including a display section, a processor, and a laser treatment unit, wherein the processor is configured to:

display a screen including a two-dimensional fundus image of an examined eye and a three-dimensional eyeball image of the examined eye on the display section;

find a second region in the two-dimensional fundus image that corresponds to a first region specified in the three-dimensional eyeball image;

display a mark indicating the second region in the two-dimensional fundus image on the display section; and control the laser treatment unit based on the first region.

What is claimed is:

1. An image display method executed by a processor, the image display method comprising:

displaying a display screen including a two-dimensional image of an examined eye and a three-dimensional image of the examined eye, wherein the three-dimensional image is an image to which the two-dimensional image is converted based on an eyeball model;

converting two-dimensional position information of a first image region specified on the two-dimensional image to three-dimensional position information; and displaying a second image region on the three-dimensional image, wherein the second region is converted from the first image region based on the three-dimensional position information.

2. The image display method of claim 1, wherein the two-dimensional image is a fundus image.

* * * * *